(12) United States Patent
Hubbard, Jr. et al.

(10) Patent No.: US 11,173,078 B2
(45) Date of Patent: Nov. 16, 2021

(54) ABSORBENT STRUCTURE

(71) Applicant: The Procter & Gamble Company, Cincinnati, OH (US)

(72) Inventors: Wade Monroe Hubbard, Jr., Wyoming, OH (US); Paul Aaron Grosse, Villa Hills, KY (US); Gerard A. Viens, Wyoming, OH (US)

(73) Assignee: The Procter & Gamble Company, Cincinnati, OH (US)

(*) Notice: Subject to any disclaimer, the term of this patent is extended or adjusted under 35 U.S.C. 154(b) by 1102 days.

(21) Appl. No.: 15/344,198

(22) Filed: Nov. 4, 2016

(65) Prior Publication Data

US 2017/0119593 A1     May 4, 2017

Related U.S. Application Data

(60) Provisional application No. 62/250,759, filed on Nov. 4, 2015.

(51) Int. Cl.
*A61F 13/15* (2006.01)
*A61F 13/53* (2006.01)
*A61F 13/534* (2006.01)

(52) U.S. Cl.
CPC ........ *A61F 13/53* (2013.01); *A61F 13/15707* (2013.01); *A61F 13/534* (2013.01);
(Continued)

(58) Field of Classification Search
CPC .. A61F 13/15707; A61F 13/53; A61F 13/534; A61F 2013/15715;
(Continued)

(56) References Cited

U.S. PATENT DOCUMENTS 1,688,341 A   10/1928   Howard
2,615,389 A   10/1952   Huebner
(Continued)

FOREIGN PATENT DOCUMENTS

CA   2250138        3/1997
CA   2331036 A1   11/1999
(Continued)

OTHER PUBLICATIONS

PCT International Search Report, PCT/US2015/037943, dated Aug. 26, 2015, 9 pages.
(Continued)

*Primary Examiner* — Bradley H Philips
(74) *Attorney, Agent, or Firm* — William E. Gallagher

(57) ABSTRACT

An absorbent structure comprising a heterogeneous mass comprising one or more enrobeable elements and one or more discrete open cell foam pieces wherein at least one of the discrete open cell foam pieces comprises a first vacuole and a second vacuole wherein the first vacuole has a first cross sectional area, wherein the second vacuole has a second cross sectional area, wherein the first vacuole enrobes a first enrobeable element, wherein the second vacuole enrobes a second enrobeable element, wherein the first enrobeable element and the second enrobeable element exhibit different surface properties.

7 Claims, 9 Drawing Sheets

(52) U.S. Cl.
CPC ............ *A61F 2013/15715* (2013.01); *A61F 2013/530817* (2013.01); *A61F 2013/530839* (2013.01); *A61F 2013/530905* (2013.01)

(58) Field of Classification Search
CPC ........ A61F 2013/530817; A61F 2013/530839; A61F 2013/530905
See application file for complete search history.

(56) References Cited

U.S. PATENT DOCUMENTS

| | | |
|---|---|---|
| 2,734,224 A | 2/1956 | Winstead |
| 2,894,732 A | 7/1959 | Taber et al. |
| 3,122,142 A * | 2/1964 | Crowe, Jr. ........ A61F 13/00038 604/369 |
| 3,274,046 A | 9/1966 | Shannon et al. |
| 3,286,992 A | 11/1966 | Armeniades et al. |
| 3,381,336 A | 5/1968 | Wells |
| 3,525,338 A | 8/1970 | Bernardin |
| 3,546,055 A | 12/1970 | Spertus |
| 3,598,742 A * | 8/1971 | Saunders ................ A24D 3/08 252/62 |
| 3,617,594 A | 11/1971 | Willy |
| 3,620,506 A | 11/1971 | So |
| 3,669,103 A | 6/1972 | Harper et al. |
| 3,669,823 A | 6/1972 | Wood |
| 3,670,731 A | 6/1972 | Harmon |
| 3,683,921 A | 8/1972 | Brooks et al. |
| 3,704,006 A | 11/1972 | Grout et al. |
| 3,804,700 A | 4/1974 | Hoey |
| 3,815,601 A | 6/1974 | Schaefer |
| 3,865,352 A | 2/1975 | Nelson et al. |
| 3,884,000 A | 5/1975 | Faleij |
| 3,908,645 A | 9/1975 | Sandvig |
| 3,982,374 A | 9/1976 | Schaefer |
| 3,994,298 A | 11/1976 | Des Marais |
| 4,026,292 A | 5/1977 | Hutchins et al. |
| 4,051,065 A | 9/1977 | Venema |
| 4,055,184 A | 10/1977 | Karami |
| 4,061,145 A | 12/1977 | DesMarais |
| 4,061,313 A | 12/1977 | Brauner et al. |
| 4,062,524 A | 12/1977 | Brauner et al. |
| 4,096,303 A | 6/1978 | Doerfling |
| 4,110,276 A | 8/1978 | Desmarais |
| 4,211,277 A | 7/1980 | Grosz-roll et al. |
| 4,321,924 A | 3/1982 | Ahr |
| 4,338,366 A | 7/1982 | Evans et al. |
| 4,357,386 A | 11/1982 | Luciano et al. |
| 4,381,783 A | 5/1983 | Elias |
| 4,416,201 A | 11/1983 | Kessler |
| 4,425,130 A | 1/1984 | Desmarais |
| 4,450,833 A | 5/1984 | Brooks et al. |
| 4,473,611 A | 9/1984 | Haq |
| 4,535,021 A | 8/1985 | Friedrich |
| 4,537,819 A | 8/1985 | Schortmann et al. |
| 4,538,920 A | 9/1985 | Drake |
| 4,550,681 A | 11/1985 | Zimmer et al. |
| 4,589,876 A | 5/1986 | Tilburg |
| 4,606,958 A | 8/1986 | Haq et al. |
| 4,664,662 A | 5/1987 | Webster |
| 4,673,402 A | 6/1987 | Weisman |
| 4,689,118 A | 8/1987 | Makoui et al. |
| 4,689,258 A | 8/1987 | Slosberg et al. |
| 4,725,628 A | 2/1988 | Garvey et al. |
| 4,737,582 A | 4/1988 | Goldman et al. |
| 4,740,700 A | 4/1988 | Shaham et al. |
| 4,758,098 A | 7/1988 | Meyer |
| 4,758,466 A * | 7/1988 | Dabi .................... A61L 15/425 442/338 |
| 4,761,203 A | 8/1988 | Vinson |
| 4,806,288 A | 2/1989 | Nowosinski et al. |
| 4,865,596 A | 9/1989 | Weisman et al. |
| 4,875,974 A | 10/1989 | Rich |
| 4,892,535 A | 1/1990 | Bjoernberg et al. |
| 4,923,454 A | 5/1990 | Seymour |
| 4,935,022 A | 6/1990 | Lash et al. |
| 4,950,264 A | 8/1990 | Osborn, III |
| 4,988,344 A | 1/1991 | Reising et al. |
| 4,988,345 A | 1/1991 | Reising |
| 4,994,037 A | 2/1991 | Bernardin |
| 5,004,760 A | 4/1991 | Patton et al. |
| 5,037,859 A | 8/1991 | Williams, Jr. et al. |
| 5,059,629 A | 10/1991 | Patton et al. |
| 5,134,007 A | 7/1992 | Reising et al. |
| 5,147,345 A | 9/1992 | Lavon |
| 5,149,334 A | 9/1992 | Berg et al. |
| 5,149,720 A | 9/1992 | Desmarais et al. |
| 5,160,345 A | 11/1992 | Bragg |
| 5,169,706 A | 12/1992 | Collier, IV et al. |
| 5,171,613 A | 12/1992 | Bok et al. |
| 5,175,046 A | 12/1992 | Nguyen |
| 5,192,606 A | 3/1993 | Proxmire |
| 5,221,710 A | 6/1993 | Markusch et al. |
| 5,221,726 A | 6/1993 | Dabi et al. |
| 5,234,423 A | 8/1993 | Alemany et al. |
| 5,244,941 A | 9/1993 | Bruckbauer et al. |
| 5,246,855 A | 9/1993 | Katinger et al. |
| 5,248,309 A | 9/1993 | Serbiak |
| 5,260,345 A | 11/1993 | DesMarais et al. |
| 5,287,707 A | 2/1994 | Kitayama |
| 5,306,734 A | 4/1994 | Bass et al. |
| 5,318,554 A | 6/1994 | Lavon et al. |
| 5,328,935 A * | 7/1994 | Van Phan ............. A61L 15/425 521/149 |
| 5,331,015 A | 7/1994 | DesMarais et al. |
| 5,338,766 A | 8/1994 | Phan et al. |
| 5,350,370 A | 9/1994 | Jackson et al. |
| 5,372,421 A | 12/1994 | Pardikes |
| 5,387,207 A | 2/1995 | Dyer et al. |
| 5,397,316 A | 3/1995 | Young |
| 5,425,725 A | 6/1995 | Tanzer |
| 5,436,066 A | 7/1995 | Chen |
| 5,454,801 A | 10/1995 | Lauritzen |
| 5,454,910 A | 10/1995 | Yoon et al. |
| 5,460,622 A | 10/1995 | Dragoo et al. |
| 5,462,538 A | 10/1995 | Korpman |
| 5,466,232 A | 11/1995 | Cadieux et al. |
| 5,486,410 A | 1/1996 | Groeger et al. |
| 5,487,736 A * | 1/1996 | Van Phan ......... A61F 13/53713 604/368 |
| 5,500,451 A | 3/1996 | Goldman et al. |
| 5,506,035 A | 4/1996 | Van Phan et al. |
| 5,518,801 A | 5/1996 | Chappell |
| 5,520,460 A | 5/1996 | Lantz |
| 5,536,264 A | 7/1996 | Hsueh et al. |
| 5,550,167 A | 8/1996 | Desmarais |
| 5,560,878 A * | 10/1996 | Dragoo ............. A61F 13/15658 264/115 |
| 5,562,646 A | 10/1996 | Goldman |
| 5,564,827 A | 10/1996 | Signer |
| 5,571,849 A * | 11/1996 | DesMarais ........... A61L 15/425 521/64 |
| 5,573,994 A | 11/1996 | Kabra et al. |
| 5,580,348 A | 12/1996 | Blaney et al. |
| 5,583,162 A | 12/1996 | Li et al. |
| 5,599,335 A | 2/1997 | Goldman |
| 5,607,550 A | 3/1997 | Akers |
| 5,620,252 A | 4/1997 | Maurer |
| 5,638,752 A | 6/1997 | Hartung et al. |
| 5,639,070 A | 6/1997 | Deckard |
| 5,647,862 A | 7/1997 | Osborn, III et al. |
| 5,647,863 A | 7/1997 | Hammons et al. |
| 5,650,222 A | 7/1997 | Desmarais et al. |
| 5,651,862 A | 7/1997 | Anderson et al. |
| 5,653,922 A | 8/1997 | Li et al. |
| 5,692,939 A * | 12/1997 | DesMarais ........... A61L 15/425 442/373 |
| 5,713,881 A | 2/1998 | Rezai |
| 5,722,482 A | 3/1998 | Buckley |
| 5,730,738 A | 3/1998 | Mcfall et al. |
| 5,732,323 A | 3/1998 | Nyrhilae |
| 5,741,581 A * | 4/1998 | DesMarais ........... A43B 1/0036 442/221 |
| 5,744,506 A | 4/1998 | Goldman et al. |

(56) References Cited

U.S. PATENT DOCUMENTS

| | | |
|---|---|---|
| 5,813,762 A | 9/1998 | Fleischli et al. |
| 5,817,704 A | 10/1998 | Shiveley et al. |
| 5,827,909 A | 10/1998 | Desmarais |
| 5,856,366 A | 1/1999 | Shiveley et al. |
| 5,858,292 A | 1/1999 | Dragoo et al. |
| 5,863,957 A | 1/1999 | Li et al. |
| 5,868,724 A | 2/1999 | Dierckes, Jr. et al. |
| 5,869,171 A | 2/1999 | Shiveley et al. |
| 5,873,869 A | 2/1999 | Hammons et al. |
| 5,900,437 A | 5/1999 | Mitchell et al. |
| 5,904,672 A | 5/1999 | Lemahieu et al. |
| 5,938,328 A | 8/1999 | Pinto et al. |
| 5,948,829 A | 9/1999 | Wallajapet et al. |
| 5,962,068 A | 10/1999 | Tsuchiya et al. |
| 5,971,603 A | 10/1999 | Davis et al. |
| 6,027,795 A | 2/2000 | Kabra et al. |
| 6,046,377 A | 4/2000 | Huntoon et al. |
| 6,083,211 A | 7/2000 | DesMarais |
| 6,103,645 A | 8/2000 | Chang et al. |
| 6,107,538 A | 8/2000 | Young et al. |
| 6,109,781 A | 8/2000 | Ogasawara et al. |
| 6,132,803 A | 10/2000 | Kelly et al. |
| 6,162,961 A | 12/2000 | Tanner et al. |
| 6,174,929 B1 | 1/2001 | Hahnle et al. |
| 6,183,587 B1 | 2/2001 | McFall et al. |
| 6,203,654 B1 | 3/2001 | McFall et al. |
| 6,231,556 B1 | 5/2001 | Osborn, III |
| 6,241,713 B1 | 6/2001 | Gross et al. |
| 6,251,479 B1 | 6/2001 | Groitzsch et al. |
| 6,261,335 B1 | 7/2001 | Kern et al. |
| 6,261,679 B1 | 7/2001 | Chen et al. |
| 6,277,104 B1 | 8/2001 | Lasko et al. |
| 6,316,688 B1 | 11/2001 | Hammons et al. |
| 6,372,953 B1 | 4/2002 | Young et al. |
| 6,399,854 B1 | 6/2002 | Vartiainen |
| 6,410,820 B1 | 6/2002 | McFall et al. |
| 6,426,445 B1 | 7/2002 | Young et al. |
| 6,455,600 B1 | 9/2002 | Hahnle et al. |
| 6,475,199 B1 | 11/2002 | Gann et al. |
| 6,486,379 B1 | 11/2002 | Chen et al. |
| 6,503,233 B1 | 1/2003 | Chen |
| 6,525,106 B1 | 2/2003 | DesMarais et al. |
| 6,551,295 B1 | 4/2003 | Schmidt et al. |
| 6,570,057 B1 | 5/2003 | Schmidt et al. |
| 6,582,411 B1 | 6/2003 | Carstens et al. |
| 6,590,136 B1 | 7/2003 | Young et al. |
| 6,600,086 B1 | 7/2003 | Mace et al. |
| 6,603,054 B2 | 8/2003 | Chen et al. |
| 6,642,430 B1 * | 11/2003 | Busam .............. A61F 13/15658 604/368 |
| 6,657,101 B1 * | 12/2003 | Malmgren ............ A61F 13/531 604/367 |
| 6,664,439 B1 * | 12/2003 | Arndt ................ A61F 13/15203 604/368 |
| 6,673,057 B1 | 1/2004 | Ehrnsperger et al. |
| 6,673,981 B1 | 1/2004 | Stroembom et al. |
| 6,676,892 B2 | 1/2004 | Das et al. |
| 6,689,935 B2 | 2/2004 | Chen et al. |
| 6,706,775 B2 | 3/2004 | Hermann et al. |
| 6,713,661 B1 | 3/2004 | Arndt et al. |
| 6,720,471 B1 | 4/2004 | Arndt et al. |
| 6,749,413 B2 | 6/2004 | Fare |
| 6,800,666 B2 | 10/2004 | Hahnle et al. |
| 6,811,842 B1 | 11/2004 | Ehrnsperger et al. |
| 6,855,424 B1 | 2/2005 | Thomas et al. |
| 6,943,200 B1 | 9/2005 | Corrand et al. |
| 6,969,548 B1 | 11/2005 | Goldfine |
| 6,989,005 B1 | 1/2006 | Lavon et al. |
| 6,989,075 B1 | 1/2006 | Kao et al. |
| 7,056,404 B2 | 6/2006 | McFall et al. |
| 7,172,801 B2 | 2/2007 | Hoying et al. |
| 7,189,888 B2 * | 3/2007 | Wang ................ A61F 13/53747 604/367 |
| 7,198,742 B2 | 4/2007 | Gerndt |
| 7,235,708 B2 | 6/2007 | Guidotti et al. |
| 7,285,576 B2 | 10/2007 | Hyde et al. |
| 7,410,683 B2 | 8/2008 | Curro et al. |
| 7,462,756 B2 | 12/2008 | Malowaniec |
| 7,507,459 B2 | 3/2009 | Turner et al. |
| 7,553,532 B2 | 6/2009 | Turner et al. |
| 7,575,635 B2 | 8/2009 | Perttilae et al. |
| 7,648,752 B2 | 1/2010 | Hoying et al. |
| 7,682,686 B2 | 3/2010 | Curro et al. |
| 7,718,243 B2 | 5/2010 | Curro et al. |
| 7,732,657 B2 | 6/2010 | Hammons et al. |
| 7,735,522 B2 | 6/2010 | Bivin et al. |
| 7,754,050 B2 | 7/2010 | Redd et al. |
| 7,789,994 B2 | 9/2010 | Hupp et al. |
| 7,838,099 B2 | 11/2010 | Curro et al. |
| 7,838,723 B1 | 11/2010 | Schmidt et al. |
| 7,850,672 B2 | 12/2010 | Guidotti et al. |
| 7,935,207 B2 | 5/2011 | Zhao et al. |
| 8,124,827 B2 | 2/2012 | Tamburro et al. |
| 8,143,472 B1 | 3/2012 | Bragd et al. |
| 8,153,226 B2 | 4/2012 | Curro |
| 8,163,132 B2 | 4/2012 | Kien |
| 8,207,393 B2 | 6/2012 | Bach |
| 8,263,820 B2 | 9/2012 | Carlucci et al. |
| 8,410,016 B2 | 4/2013 | Cote et al. |
| 8,426,670 B2 | 4/2013 | Nagasuna et al. |
| 8,641,267 B2 | 2/2014 | Baeuerle et al. |
| 8,674,169 B2 | 3/2014 | Brennan et al. |
| 8,707,717 B2 | 4/2014 | Fox et al. |
| 8,708,723 B2 | 4/2014 | Stoltz |
| 8,728,049 B2 | 5/2014 | Hammons et al. |
| 8,906,404 B2 | 12/2014 | Wellings |
| 9,408,761 B2 | 8/2016 | Xu et al. |
| 9,566,196 B2 | 2/2017 | Carlucci et al. |
| 9,907,709 B2 | 3/2018 | Seitz et al. |
| 9,956,586 B2 | 5/2018 | Pinyayev et al. |
| 9,974,424 B2 | 5/2018 | Roe et al. |
| 9,993,836 B2 | 6/2018 | Mcneil et al. |
| 10,016,779 B2 | 7/2018 | Mcneil et al. |
| 10,028,867 B2 | 7/2018 | Ehrnsperger et al. |
| 10,045,888 B2 | 8/2018 | Strube et al. |
| 10,045,890 B2 | 8/2018 | Hubbard, Jr. |
| 10,131,724 B2 | 11/2018 | Merrigan et al. |
| 10,357,588 B2 | 7/2019 | Thompson, Jr. et al. |
| 10,583,053 B2 | 3/2020 | Robles et al. |
| 10,729,600 B2 * | 8/2020 | Bewick-Sonntag ........................ A61F 13/534 |
| 2001/0000796 A1 | 5/2001 | Osborn et al. |
| 2001/0024716 A1 | 9/2001 | Chen et al. |
| 2001/0033527 A1 | 10/2001 | Smith |
| 2001/0041876 A1 | 11/2001 | Creagan et al. |
| 2001/0047456 A1 | 11/2001 | Schrobenhauzer et al. |
| 2002/0034911 A1 | 3/2002 | Tsuchiya et al. |
| 2002/0057627 A1 | 5/2002 | Schubert et al. |
| 2002/0064087 A1 | 5/2002 | Catalfamo et al. |
| 2002/0095132 A1 | 7/2002 | Ashton et al. |
| 2002/0099348 A1 | 7/2002 | Ollivier et al. |
| 2002/0118598 A1 | 8/2002 | Schuchardt |
| 2002/0123283 A1 | 9/2002 | Dyer et al. |
| 2002/0132106 A1 * | 9/2002 | Dyer ........................ B32B 5/18 428/317.9 |
| 2002/0143310 A1 | 10/2002 | Malmgren et al. |
| 2002/0177831 A1 | 11/2002 | Daley et al. |
| 2003/0008108 A1 | 1/2003 | Shizuno et al. |
| 2003/0015003 A1 | 1/2003 | Fisler et al. |
| 2003/0084788 A1 | 5/2003 | Fraser |
| 2003/0093050 A1 | 5/2003 | Baker |
| 2003/0097103 A1 | 5/2003 | Horney |
| 2003/0120231 A1 | 6/2003 | Wang |
| 2003/0134918 A1 | 7/2003 | Ko et al. |
| 2003/0165080 A1 | 9/2003 | Pinyayev et al. |
| 2003/0181884 A1 | 9/2003 | Carstens et al. |
| 2003/0191204 A1 | 10/2003 | Hermann et al. |
| 2003/0211248 A1 * | 11/2003 | Ko .................... A61F 13/15658 427/385.5 |
| 2003/0220039 A1 * | 11/2003 | Chen ..................... A61F 13/53 442/327 |
| 2004/0037161 A1 | 2/2004 | Honda et al. |
| 2004/0054341 A1 | 3/2004 | Kellenberger et al. |
| 2004/0054342 A1 | 3/2004 | Newbill et al. |

(56) References Cited

U.S. PATENT DOCUMENTS

| | | |
|---|---|---|
| 2004/0121905 A1 | 6/2004 | Ranganathan et al. |
| 2004/0159616 A1 | 8/2004 | Cohee et al. |
| 2004/0193129 A1 | 9/2004 | Guidotti et al. |
| 2004/0204554 A1 | 10/2004 | Ko et al. |
| 2004/0214961 A1 | 10/2004 | Gartner et al. |
| 2004/0218469 A1 | 11/2004 | Unterlander et al. |
| 2004/0227275 A1 | 11/2004 | Maschino et al. |
| 2004/0229008 A1 | 11/2004 | Hoying |
| 2004/0242097 A1 | 12/2004 | Hasenoehrl |
| 2005/0087292 A1 | 4/2005 | McFall et al. |
| 2005/0123726 A1 | 6/2005 | Broering et al. |
| 2005/0125923 A1 | 6/2005 | Benjamin et al. |
| 2005/0136224 A1 | 6/2005 | Nickel et al. |
| 2005/0185508 A1 | 8/2005 | Schulz-hanke et al. |
| 2005/0250866 A1 | 11/2005 | Champ et al. |
| 2005/0266230 A1* | 12/2005 | Hill .................. B32B 5/30 428/317.9 |
| 2006/0008419 A1 | 1/2006 | Hissink et al. |
| 2006/0052269 A1 | 3/2006 | Panandiker et al. |
| 2006/0058750 A1 | 3/2006 | Di Girolamo et al. |
| 2006/0121811 A1 | 6/2006 | Mangold et al. |
| 2006/0127498 A1 | 6/2006 | Sugiura |
| 2006/0189240 A1 | 8/2006 | Taylor et al. |
| 2006/0193985 A1 | 8/2006 | Mcneil et al. |
| 2006/0286343 A1 | 12/2006 | Curro |
| 2007/0027435 A1 | 2/2007 | Nakagawa et al. |
| 2007/0043330 A1 | 2/2007 | Lankhof |
| 2007/0088308 A1 | 4/2007 | Ehrnsperger et al. |
| 2007/0116926 A1 | 5/2007 | Hoying et al. |
| 2007/0142803 A1 | 6/2007 | Soerens et al. |
| 2007/0225669 A1 | 9/2007 | Dyer |
| 2008/0056064 A1 | 3/2008 | Tanaka |
| 2008/0076844 A1 | 3/2008 | Van Sumeren et al. |
| 2008/0217809 A1 | 9/2008 | Zhao |
| 2008/0221538 A1 | 9/2008 | Zhao |
| 2008/0281287 A1 | 11/2008 | Marcelo et al. |
| 2009/0036851 A1 | 2/2009 | Carlucci |
| 2009/0036854 A1 | 2/2009 | Guidotti et al. |
| 2009/0079107 A1 | 3/2009 | Abiru |
| 2009/0103393 A1 | 4/2009 | Moser et al. |
| 2009/0118689 A1 | 5/2009 | Lawson et al. |
| 2009/0122638 A1 | 5/2009 | Sato et al. |
| 2009/0266478 A1 | 10/2009 | Schafer et al. |
| 2009/0270827 A1 | 10/2009 | Gundersen et al. |
| 2010/0003391 A1 | 1/2010 | Melnyczuk |
| 2010/0035014 A1 | 2/2010 | Hammons |
| 2010/0110826 A1 | 5/2010 | D Herde |
| 2010/0126366 A1 | 5/2010 | Kasper et al. |
| 2010/0162888 A1 | 7/2010 | Blucher et al. |
| 2010/0202248 A1 | 8/2010 | Hirschberg et al. |
| 2010/0228209 A1 | 9/2010 | Carlucci et al. |
| 2010/0247844 A1 | 9/2010 | Curro |
| 2010/0262104 A1 | 10/2010 | Carlucci et al. |
| 2010/0280479 A1 | 11/2010 | Lindqvist et al. |
| 2010/0307665 A1 | 12/2010 | Mccutchen |
| 2010/0310837 A1 | 12/2010 | Bond et al. |
| 2011/0070423 A1 | 3/2011 | Jayakody et al. |
| 2011/0080801 A1 | 4/2011 | Georg et al. |
| 2011/0092936 A1* | 4/2011 | Kunimoto ............ D01F 6/70 604/370 |
| 2011/0114245 A1 | 5/2011 | Nhan et al. |
| 2011/0128814 A1 | 6/2011 | Hanada |
| 2011/0150703 A1 | 6/2011 | Castro et al. |
| 2011/0174430 A1 | 7/2011 | Zhao et al. |
| 2011/0176965 A1 | 7/2011 | Castro et al. |
| 2011/0196330 A1 | 8/2011 | Hammons |
| 2011/0305104 A1 | 12/2011 | Mcguire et al. |
| 2011/0310697 A1 | 12/2011 | Hirschberg |
| 2011/0313384 A1 | 12/2011 | Akiyama |
| 2012/0001122 A1 | 1/2012 | Wattelbled |
| 2012/0077992 A1 | 3/2012 | Hutter et al. |
| 2012/0101460 A1 | 4/2012 | Ehmke et al. |
| 2012/0106290 A1 | 5/2012 | Meijer et al. |
| 2012/0108692 A1 | 5/2012 | Dyer |
| 2012/0134232 A1 | 5/2012 | Schneider |
| 2012/0193841 A1 | 8/2012 | Wang et al. |
| 2012/0201806 A1 | 8/2012 | Silverstein et al. |
| 2012/0209230 A1 | 8/2012 | Mansfield |
| 2012/0222567 A1 | 9/2012 | Mcneil et al. |
| 2012/0222568 A1 | 9/2012 | Byrne et al. |
| 2012/0237606 A1 | 9/2012 | Wellings |
| 2012/0296296 A1 | 11/2012 | Di Cintio et al. |
| 2012/0302440 A1 | 11/2012 | Theliander et al. |
| 2012/0308780 A1 | 12/2012 | Rottger et al. |
| 2012/0316523 A1 | 12/2012 | Hippe |
| 2012/0323201 A1 | 12/2012 | Bissah et al. |
| 2013/0006205 A1 | 1/2013 | Mckiernan et al. |
| 2013/0018341 A1 | 1/2013 | Carlucci et al. |
| 2013/0021868 A1 | 1/2013 | Doolin et al. |
| 2013/0079741 A1 | 3/2013 | Nakashita et al. |
| 2013/0107660 A1 | 5/2013 | Pappalardo |
| 2013/0218115 A1 | 8/2013 | Katsuragawa et al. |
| 2013/0253463 A1 | 9/2013 | Mansfield |
| 2013/0324959 A1 | 12/2013 | Ashraf et al. |
| 2014/0050886 A1 | 2/2014 | Burgin et al. |
| 2014/0141970 A1 | 5/2014 | Konishi et al. |
| 2014/0163503 A1 | 6/2014 | Arizti et al. |
| 2014/0228796 A1 | 8/2014 | Burvall et al. |
| 2014/0276518 A1 | 9/2014 | Varona et al. |
| 2014/0295134 A1 | 10/2014 | Wood et al. |
| 2014/0295135 A1 | 10/2014 | Thompson, Jr. et al. |
| 2014/0296817 A1 | 10/2014 | Van Malderen |
| 2014/0303582 A1 | 10/2014 | Wright et al. |
| 2014/0366293 A1 | 12/2014 | Roe |
| 2015/0080823 A1 | 3/2015 | Thompson et al. |
| 2015/0119837 A1 | 4/2015 | Thompson, Jr. et al. |
| 2015/0179750 A1 | 6/2015 | Calafut et al. |
| 2015/0245957 A1 | 9/2015 | Hashino et al. |
| 2015/0246484 A1 | 9/2015 | Hirschberg |
| 2015/0298075 A1 | 10/2015 | Glanville |
| 2015/0313770 A1* | 11/2015 | Hubbard, Jr. ......... A61F 13/534 604/369 |
| 2015/0313771 A1 | 11/2015 | Bergstrom et al. |
| 2015/0328059 A1 | 11/2015 | Robles et al. |
| 2015/0335498 A1* | 11/2015 | Hubbard, Jr. ......... A61L 15/425 604/378 |
| 2015/0343757 A1 | 12/2015 | Byrne et al. |
| 2015/0343760 A1 | 12/2015 | Byrne et al. |
| 2015/0351976 A1 | 12/2015 | Viens |
| 2015/0374560 A1 | 12/2015 | Hubbard, Jr. |
| 2015/0374561 A1* | 12/2015 | Hubbard, Jr. ......... A61L 15/425 604/369 |
| 2015/0374876 A1 | 12/2015 | Hubbard, Jr. |
| 2016/0160900 A1 | 6/2016 | Milanowski |
| 2016/0175787 A1 | 6/2016 | Merrigan et al. |
| 2016/0287452 A1 | 10/2016 | Hubbard, Jr. |
| 2016/0346805 A1 | 12/2016 | Mcneil et al. |
| 2016/0375458 A1 | 12/2016 | Mcneil et al. |
| 2017/0071795 A1 | 3/2017 | Bewick-sonntag et al. |
| 2017/0119587 A1 | 5/2017 | Bewick-sonntag |
| 2017/0119588 A1 | 5/2017 | Bewick-sonntag |
| 2017/0119589 A1 | 5/2017 | Bewick-sonntag |
| 2017/0119594 A1 | 5/2017 | Bewick-sonntag |
| 2017/0119595 A1 | 5/2017 | Carla |
| 2017/0119596 A1 | 5/2017 | Bewick-sonntag |
| 2017/0119597 A1 | 5/2017 | Bewick-sonntag |
| 2017/0119598 A1 | 5/2017 | Bewick-sonntag |
| 2017/0252708 A1 | 9/2017 | Pappalardo |
| 2017/0319401 A1 | 11/2017 | Ludher |
| 2017/0319402 A1 | 11/2017 | Morrow |
| 2017/0319403 A1 | 11/2017 | Bewick-sonntag |
| 2017/0319404 A1 | 11/2017 | Bewick-sonntag |
| 2017/0321083 A1 | 11/2017 | Fenn et al. |
| 2017/0360618 A1 | 12/2017 | Mullane |
| 2018/0110660 A1 | 4/2018 | Bewick-sonntag |
| 2018/0168884 A1 | 6/2018 | Hubbard, Jr. et al. |
| 2018/0169832 A1 | 6/2018 | Viens et al. |
| 2018/0228656 A1 | 8/2018 | Schneider et al. |
| 2018/0228666 A1 | 8/2018 | Trinkaus et al. |
| 2018/0228667 A1 | 8/2018 | Schneider et al. |
| 2018/0228668 A1 | 8/2018 | Schneider et al. |
| 2018/0228669 A1 | 8/2018 | Schneider et al. |

(56) References Cited

U.S. PATENT DOCUMENTS

| | | |
|---|---|---|
| 2018/0318150 A1 | 11/2018 | Bewick-sonntag et al. |
| 2018/0333737 A1 | 11/2018 | Mcneil et al. |
| 2020/0268574 A1 | 8/2020 | Bewick-sonntag et al. |

FOREIGN PATENT DOCUMENTS

| | | |
|---|---|---|
| CN | 1845715 A | 10/2006 |
| DE | 2649974 A1 | 5/1977 |
| DE | 202014002444 U1 | 4/2014 |
| EP | 0138427 A1 | 4/1985 |
| EP | 0278476 | 2/1988 |
| EP | 0471114 A2 | 2/1992 |
| EP | 0532002 A1 | 3/1993 |
| EP | 0794751 | 11/1995 |
| EP | 1061966 | 3/1999 |
| EP | 1048276 A1 | 11/2000 |
| EP | 1267769 | 1/2003 |
| EP | 1048625 B1 | 1/2004 |
| EP | 1605881 | 1/2004 |
| EP | 1139951 | 10/2004 |
| EP | 1358894 | 11/2013 |
| FR | 2822045 | 9/2002 |
| GB | 1570485 | 7/1980 |
| GB | 2326828 | 1/1999 |
| JP | S5832641 A | 2/1983 |
| JP | H02239863 A | 9/1990 |
| JP | H03241079 A | 10/1991 |
| JP | H0440948 A | 2/1992 |
| JP | 2000107216 A | 4/2000 |
| JP | 2002065741 A | 3/2002 |
| JP | 2003220660 A | 8/2003 |
| JP | 2005185559 A | 7/2005 |
| JP | 2006175076 A | 7/2006 |
| JP | 2013180171 A | 9/2013 |
| JP | 2016116714 A | 6/2016 |
| WO | 9510995 A1 | 4/1995 |
| WO | WO9611714 | 4/1996 |
| WO | 9612460 A1 | 5/1996 |
| WO | 9616624 A2 | 6/1996 |
| WO | 1996017681 | 6/1996 |
| WO | 9623466 A1 | 8/1996 |
| WO | 1998022065 | 5/1998 |
| WO | 1998022067 | 5/1998 |
| WO | 1999025393 | 5/1998 |
| WO | 1999025394 | 5/1998 |
| WO | 1998024832 | 6/1998 |
| WO | 1998025999 | 6/1998 |
| WO | 1999025745 | 5/1999 |
| WO | 1999025748 | 5/1999 |
| WO | 9926670 A1 | 6/1999 |
| WO | WO9945878 | 9/1999 |
| WO | WO9947184 | 9/1999 |
| WO | WO9955269 | 11/1999 |
| WO | 0039201 | 12/1999 |
| WO | WO0000138 | 1/2000 |
| WO | WO0000136 | 12/2000 |
| WO | WO0059438 | 12/2000 |
| WO | WO0078369 | 12/2000 |
| WO | 0124754 A1 | 4/2001 |
| WO | WO2001068022 | 9/2001 |
| WO | 0224132 A2 | 3/2002 |
| WO | WO2003026707 | 10/2003 |
| WO | 03092568 A1 | 11/2003 |
| WO | WO2004084784 | 10/2004 |
| WO | WO2004084785 | 10/2004 |
| WO | 2007032810 | 3/2007 |
| WO | 2007113627 A1 | 10/2007 |
| WO | 2008107846 A1 | 9/2008 |
| WO | 2010118320 A2 | 10/2010 |
| WO | 2011038084 A1 | 3/2011 |
| WO | 2013180937 A1 | 12/2013 |
| WO | 2014205015 A1 | 12/2014 |
| WO | 2015200777 A1 | 12/2015 |

OTHER PUBLICATIONS

PCT International Search Report, PCT/US2015/029199, dated Jul. 21, 2015, 12 pages.
PCT International Search Report, PCT/US2015/032154, dated Aug. 26, 2015, 10 pages.
PCT International Search Report, PCT/US2016/060584, dated Feb. 3, 20127 12 pages.
All Office Actions, U.S. Appl. No. 14/704,110.
All Office Actions, U.S. Appl. No. 14/715,984.
All Office Actions, U.S. Appl. No. 14/750,596.
All Office Actions, U.S. Appl. No. 15/084,902.
All Office Actions, U.S. Appl. No. 15/343,989.
All Office Actions, U.S. Appl. No. 15/344,050.
All Office Actions, U.S. Appl. No. 15/344,090.
All Office Actions, U.S. Appl. No. 15/344,117.
All Office Actions, U.S. Appl. No. 15/344,177.
All Office Actions, U.S. Appl. No. 15/344,221.
All Office Actions, U.S. Appl. No. 15/344,239.
All Office Actions, U.S. Appl. No. 15/344,292.
All Office Actions, U.S. Appl. No. 15/587,455.
All Office Actions, U.S. Appl. No. 15/843,619.
All Office Actions, U.S. Appl. No. 11/389,706.
All Office Actions, U.S. Appl. No. 14/307,892.
All Office Actions, U.S. Appl. No. 14/699,011.
All Office Actions, U.S. Appl. No. 14/751,969.
All Office Actions, U.S. Appl. No. 14/937,362.
All Office Actions, U.S. Appl. No. 14/974,551.
All Office Actions, U.S. Appl. No. 15/078,132.
All Office Actions, U.S. Appl. No. 15/194,894.
All Office Actions, U.S. Appl. No. 15/344,255.
All Office Actions, U.S. Appl. No. 15/587,545.
All Office Actions, U.S. Appl. No. 15/587,577.
All Office Actions, U.S. Appl. No. 15/587,894.
All Office Actions, U.S. Appl. No. 15/587,876.
All Office Actions, U.S. Appl. No. 15/843,655.
All Office Actions, U.S. Appl. No. 15/969,951.
All Office Actions, U.S. Appl. No. 15/980,281.
All Office Actions, U.S. Appl. No. 15/587,908.
All Office Actions, U.S. Appl. No. 16/863,166.
All Office Actions, U.S. Appl. No. 09/258,889.
Estes, W. et al, "Estimation of Dissolution Rate fromIn-Vivo Studies of Synthetic Fibers," Inhalation Toxicology, vol. 12, No. 11, pp. 1037-1054.
Fowkes, Determination of Interfacial Tensions, Contact Angles,and Dispersion Forces in SurfAces by AssumingAdditivity OfIntermolecular Interactions in Surf Aces, Communications to theEditor, vol. 66, p. 382.
Fowkes, Attractive Forces at Interfaces, The Interface Symposium-5, Industrial and Engineering Chemistry, vol. 58, No. 12, Dec. 1964, pp. 40-52.
Grate, J.W. et al, "Correlation of Oil-Water and Air-Water Contact Angles of Diverse Silanized Surfaces and Relationship to Fluid Interfacial Tensions", vol. 28, https://pubs.acs.org/sharing-guidelines, 2012, pp. 7182-7188.
International Search Report and Written Opinion; Application Ser. No. PCT /US2016/060588; dated Feb. 3, 2017, 14 pages.
International Search Report and Written Opinion; Application Ser. No. PCT/US/2016/060561; dated Feb. 28, 2017, 13 pages.
International Search Report and Written Opinion; Application Ser. No. PCT/US2016/060553; dated Feb. 8, 2017, 12 pages.
International Search Report and Written Opinion; Application Ser. No. PCT/US2016/060565; dated Mar. 3, 2017, 12 pages.
International Search Report and Written Opinion; Application Ser. No. PCT/US2016/060568; dated Feb. 20, 2017, 11 pages.
International Search Report and Written Opinion; Application Ser. No. PCT/US2016/060581; dated Feb. 3, 2017, 11 pages.
International Search Report and Written Opinion; Application Ser. No. PCT/US2016/060589; dated Feb. 3, 2017, 13 pages.
International Search Report and Written Opinion; Application Ser. No. PCT/US2016/060590; dated Feb. 6, 2017, 12 pages.
International Search Report and Written Opinion; Application Ser. No. PCT/US2016/060593; dated Feb. 28, 2017, 12 pages.

(56) References Cited

OTHER PUBLICATIONS

Lepine, O. et al, "Preparation of Macrocellular PU-PS Interpenetrating Networks", Polymer, Elsevier Science Publishers B.V., GB, vol. 46, No. 23, Nov. 14, 2005, pp. 9653-9663.
Merriam Webster, "Definition of Enrobe" 2020, 5 pages.
Merriam Webster,"Definition of Planar", 2020, 7 pages.
Somos, "NanoTool Product Data Sheet", 2012, 2 pages.
Somos, "Somos Nanotool Now Commercially Available—Autocentral.com", https://www.autocentral.com/doc/somos-nanotool-now-commercially-available-0001, 2006, 2 pages.
Somos, Somos NanoTool Now Commercially Available, https://www.digitalengineering247.com/article/somos-nanotool-now-commercially-available; Digital Engineering, Dec. 18, 2006, 4 pages.
SOMOS, "NanoTool MSDS Data Sheet", 2016, 5 pages.
Surface Energy Data for PTFE: Polytetrafluoroethylene, CAS # 9002-84-0, ©2009, Diversified Enterprises, 3 pages.
Vaezi, M.et al, "A review on 3D micro-additive manufacturing technologies", Int J Adv Manufacturing Technology, vol. 67, 2013, pp. 1721-1754.

\* cited by examiner

ABSORBENT STRUCTURE

FIELD OF THE INVENTION

The present invention relates to absorbent structures useful in absorbent articles such as diapers, incontinent briefs, training pants, diaper holders and liners, sanitary hygiene garments, and the like. Specifically, the present invention relates to an absorbent structure that exhibits desirable consumer properties.

BACKGROUND OF THE INVENTION

Open celled foams are used for their absorbent properties. Open celled foams include latex polymer foams, polyurethane foams, and foams created by polymerizing an emulsion. One type of an open celled foam is created from an emulsion that is a dispersion of one liquid in another liquid and generally is in the form of a water-in-oil mixture having an aqueous or water phase dispersed within a substantially immiscible continuous oil phase. Water-in-oil (or oil in water) emulsions having a high ratio of dispersed phase to continuous phase are known in the art as High Internal Phase Emulsions, also referred to as "HIPE" or HIPEs. Different foams may be chosen due to specific properties.

Traditionally, open celled foams are polymerized in a continuous sheet or in a tubular reaction. Either process represents that one must use polymerized open celled foam in a continuous form or break up the polymerized open celled foam to make open celled foam pieces.

During processing, one layer of foam may be laid down upon a different layer of foam. This may be done to create a core that has two different pore-size ranges. One pore size may be optimized for acquisition while the other pore size may be optimized for storage.

Ultimately, in regards to an absorbent core, the current process represents using a core made solely of foam or a core that uses pieces of foam placed into or onto another material. If a core with two different pore sizes is desired, this represents having two different processes, each targeting the desired pore size.

Therefore there exists a need to create a foam that has different pore-size ranges within the same foam without using either two different compositions or two different systems that are combined to create the dual pore size structure. Further, while creating a foam that has different pore-size ranges within the same foam, there exists a need to be able to dial in the vacuole size at specific portion of the foam such that the overall product can exhibit the desired properties. Further, there exists a need to create an absorbent foam that penetrates a fibrous system at controlled levels to create the desired overall absorbent stratum (layer).

SUMMARY OF THE INVENTION

A heterogeneous mass is disclosed. The heterogeneous mass comprising a longitudinal axis, a lateral axis, a vertical axis, two or more enrobeable elements and one or more discrete open cell foam pieces wherein at least one of the discrete open cell foam pieces comprises a first vacuole, wherein the first vacuole has a first cross sectional area, wherein the first vacuole enrobes a first enrobeable element, wherein the first enrobeable element and the second enrobeable element exhibit different surface properties or physical geometries.

A heterogeneous mass is further disclosed. The heterogeneous mass comprising a longitudinal axis, a lateral axis, a vertical axis, one or more enrobeable elements and one or more discrete open cell foam pieces wherein at least one of the discrete open cell foam pieces comprises a first vacuole and a second vacuole wherein the first vacuole has a first cross sectional area, wherein the second vacuole has a second cross sectional area, wherein the first vacuole enrobes a first enrobeable element, wherein the second vacuole enrobes a second enrobeable element, wherein the first enrobeable element and the second enrobeable element exhibit different surface properties or physical geometries.

A method of creating vacuoles within a heterogeneous mass is further disclosed. The method comprising coating one or more enrobeable element with a surfactant to form a coated enrobeable element, enrobing one or more enrobeable elements comprising the coated enrobeable element with a high internal phase emulsion, polymerizing the high internal phase emulsion to form a heterogeneous mass containing a discrete open cell foam piece comprising a vacuole.

BRIEF DESCRIPTION OF THE DRAWINGS

While the specification concludes with claims particularly pointing out and distinctly claiming the subject matter of the present invention, it is believed that the invention can be more readily understood from the following description taken in connection with the accompanying drawings, in which:

DETAILED DESCRIPTION OF THE INVENTION

Figure 1:
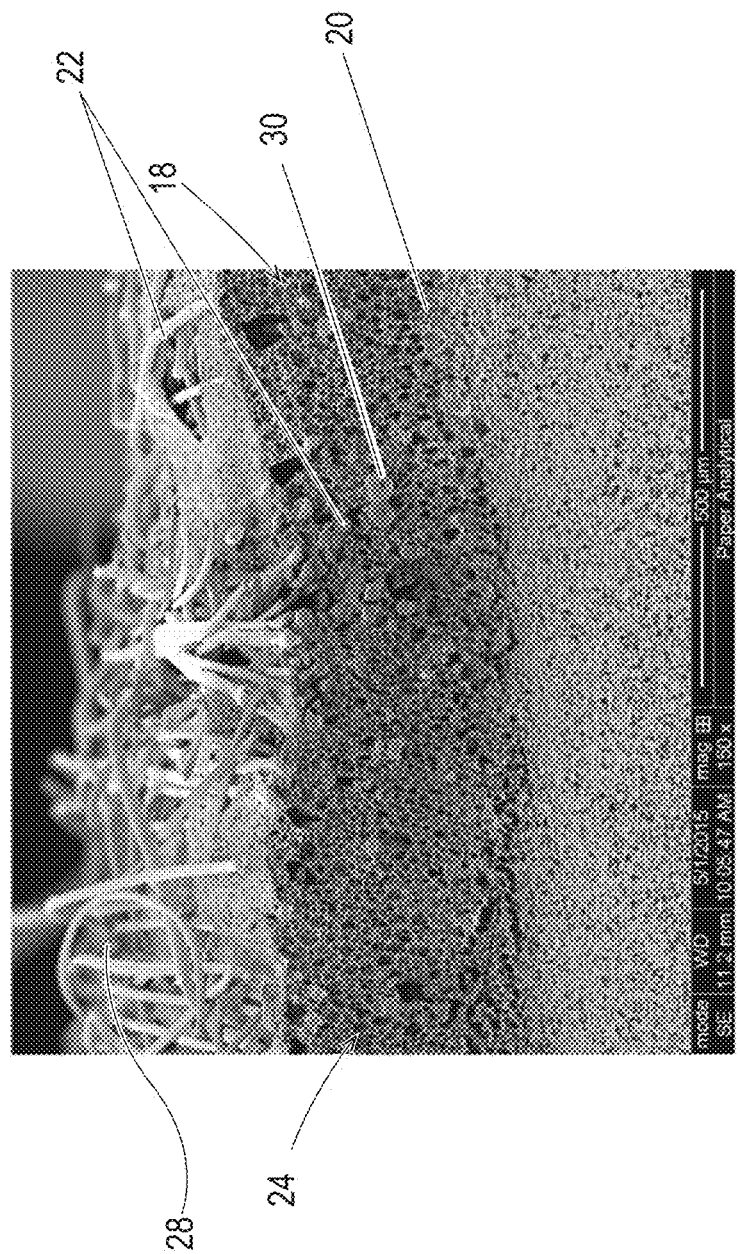
FIG. 1 is an SEM of a representative HIPE foam piece enrobing one or more fibers.

As used herein, the term "bicomponent fibers" refers to fibers which have been formed from at least two different polymers extruded from separate extruders but spun together to form one fiber. Bicomponent fibers are also sometimes referred to as conjugate fibers or multicomponent fibers. The polymers are arranged in substantially constantly positioned distinct zones across the cross-section of the bicomponent fibers and extend continuously along the length of the bicomponent fibers. The configuration of such a bicomponent fiber may be, for example, a sheath/core arrangement wherein one polymer is surrounded by another, or may be a side-by-side arrangement, a pie arrangement, or an "islands-in-the-sea" arrangement.

As used herein, the term "biconstituent fibers" refers to fibers which have been formed from at least two polymers extruded from the same extruder as a blend. Biconstituent fibers do not have the various polymer components arranged in relatively constantly positioned distinct zones across the cross-sectional area of the fiber and the various polymers are usually not continuous along the entire length of the fiber, instead usually forming fibrils which start and end at random. Biconstituent fibers are sometimes also referred to as multiconstituent fibers.

In the following description the term "cellulose fibers" is used. Cellulose fibers comprise naturally occurring fibers based on cellulose, such as, for example cotton, linen, etc. Wood pulp fibers are one example of cellulose fibers according to the present invention. Man-made fibers derived from cellulose, such as regenerated cellulose, e.g. viscose or partially or fully acetylated cellulose derivatives (e.g. cellulose acetate or triacetate), are also considered as cellulose fibers according to the present invention.

The term "disposable" is used herein to describe articles, which are not intended to be laundered or otherwise restored or reused as an article (i.e. they are intended to be discarded after a single use and possibly to be recycled, composted or otherwise disposed of in an environmentally compatible manner). The absorbent article comprising an absorbent structure according to the present invention can be for example a sanitary napkin, a panty liner, an adult incontinence product, a diaper, or any other product designed to absorb a bodily exudate. The absorbent structure of the present invention will be herein described in the context of a typical absorbent article, such as, for example, a sanitary napkin. Typically, such articles may comprise a liquid pervious topsheet, a backsheet and an absorbent core intermediate the topsheet and the backsheet.

As used herein, an "enrobeable element" refers to an element that may be enrobed by the foam. The enrobeable element may be, for example, a fiber, a group of fibers, a tuft, or a section of a film between two apertures. It is understood that other elements are contemplated by the present invention.

A "fiber" as used herein, refers to any material that may be part of a fibrous structure. Fibers may be natural or synthetic. Fibers may be absorbent or non-absorbent.

A "fibrous structure" as used herein, refers to materials which may be broken into one or more fibers. A fibrous structure can be absorbent or adsorbent. A fibrous structure may exhibit capillary action as well as porosity and permeability.

As used herein, the term "meltblowing" refers to a process in which fibers are formed by extruding a molten thermoplastic material through a plurality of fine, usually circular, die capillaries as molten threads or filaments into converging high velocity, usually heated, gas (for example air) streams which attenuate the filaments of molten thermoplastic material to reduce their diameter. Thereafter, the meltblown fibers are carried by the high velocity gas stream and are deposited on a collecting surface, often while still tacky, to form a web of randomly dispersed meltblown fibers.

As used herein, the term "monocomponent" fiber refers to a fiber formed from one or more extruders using only one polymer. This is not meant to exclude fibers formed from one polymer to which small amounts of additives have been added for coloration, antistatic properties, lubrication, hydrophilicity, etc. These additives, for example titanium dioxide for coloration, are generally present in an amount less than about 5 weight percent and more typically about 2 weight percent.

As used herein, the term "non-round fibers" describes fibers having a non-round cross-section, and includes "shaped fibers" and "capillary channel fibers." Such fibers may be solid or hollow, and they may be tri-lobal, delta-shaped, and may be fibers having capillary channels on their outer surfaces. The capillary channels may be of various cross-sectional shapes such as "U-shaped", "H-shaped", "C-shaped" and "V-shaped". One practical capillary channel fiber is T-401, designated as 4DG fiber available from Fiber Innovation Technologies, Johnson City, Tenn. T-401 fiber is a polyethylene terephthalate (PET polyester).

As used herein, the term "nonwoven web" refers to a web having a structure of individual fibers or threads which are interlaid, but not in a repeating pattern as in a woven or knitted fabric, which do not typically have randomly oriented fibers. Nonwoven webs or fabrics have been formed from many processes, such as, for example, electro-spinning, meltblowing processes, spunbonding processes, spunlacing processes, hydroentangling, airlaying, and bonded carded web processes, including carded thermal bonding. The basis weight of nonwoven fabrics is usually expressed in grams per square meter (gsm). The basis weight of the laminate web is the combined basis weight of the constituent layers and any other added components. Fiber diameters are usually expressed in microns; fiber size may also be expressed in denier, which is a unit of weight per length of fiber. The basis weight of laminate webs suitable for use in an article of the present invention may range from about 10 gsm to about 100 gsm, depending on the ultimate use of the web.

As used herein, the term "polymer" generally includes, but is not limited to, homopolymers, copolymers, such as for example, block, graft, random and alternating copolymers, terpolymers, etc., and blends and modifications thereof. In addition, unless otherwise specifically limited, the term "polymer" includes all possible geometric configurations of the material. The configurations include, but are not limited to, isotactic, atactic, syndiotactic, and random symmetries.

As used herein, "spunbond fibers" refers to small diameter fibers which are formed by extruding molten thermoplastic material as filaments from a plurality of fine, usually circular capillaries of a spinneret with the diameter of the extruded filaments then being rapidly reduced. Spunbond fibers are generally not tacky when they are deposited on a collecting surface. Spunbond fibers are generally continuous and have average diameters (from a sample size of at least 10 fibers) larger than 7 microns, and more particularly, between about 10 and 40 microns.

As used herein, a "strata" or "stratum" relates to one or more layers wherein the components within the stratum are intimately combined without the necessity of an adhesive, pressure bonds, heat welds, a combination of pressure and heat bonding, hydro-entangling, needlepunching, ultrasonic bonding, or similar methods of bonding known in the art such that individual components may not be wholly separated from the stratum without affecting the physical structure of the other components. The skilled artisan should understand that while separate bonding is unnecessary between the strata, bonding techniques could be employed to provide additional integrity depending on the intended use.

As used herein, a "tuft" or chad relates to discrete integral extensions of the fibers of a nonwoven web. Each tuft may comprise a plurality of looped, aligned fibers extending outwardly from the surface of the web. Each tuft may comprise a plurality of non-looped fibers that extend outwardly from the surface of the web. Each tuft may comprise a plurality of fibers which are integral extensions of the fibers of two or more integrated nonwoven webs.

While particular embodiments of the present invention have been illustrated and described, it would be obvious to those skilled in the art that various other changes and modifications may be made without departing from the spirit and scope of the invention.

GENERAL SUMMARY

The present invention relates to an absorbent structure that is a heterogeneous mass having one or more enrobeable elements and one or more discrete open cell foam pieces wherein at least one of the discrete open cell foam pieces comprises a first vacuole and a second vacuole wherein the first vacuole has a first cross sectional area, wherein the second vacuole has a second cross sectional area, wherein the first vacuole enrobes a first enrobeable element, wherein the second vacuole enrobes a second enrobeable element, wherein the first enrobeable element and the second enrobeable element exhibit different surface properties. The present invention relates to an absorbent structure that is a heterogeneous mass having one or more enrobeable elements and one or more discrete open cell foam pieces wherein at least one of the discrete open cell foam pieces comprises a first vacuole, wherein the first vacuole enrobes a first enrobeable element, and wherein the at least one of the open cell foam pieces comprises a second enrobeable element, and wherein the open cell foam enrobes the second enrobeable element without the presence of a vacuole. The absorbent structure single stratum may comprise one or more absorbent layers. The absorbent structure single stratum may be a heterogeneous mass.

The present invention relates to an absorbent structure that is a heterogeneous mass comprising one or more enrobeable elements and one or more discrete open cell foam pieces that have both pores and one or more vacuoles. The area at any given cross section of a vacuole are a magnitude of the area at any given cross section of a pore. The vacuoles may contain enrobeable elements and serve as areas wherein the open cell foam enrobes the enrobeable elements. The enrobeable elements may be treated with a surfactant to manipulate the vacuole size. The enrobeable elements may exhibit properties that affect the vacuole size. The absorbent structure may be a heterogeneous mass. The heterogeneous mass has a depth, a width, and a height. The absorbent structure may be used as any part of an absorbent article including, for example, a part of an absorbent core, as an absorbent core, and/or as a topsheet for absorbent articles such as sanitary napkins, panty liners, tampons, interlabial devices, wound dressings, diapers, adult incontinence articles, and the like, which are intended for the absorption of body fluids, such as menses or blood or vaginal discharges or urine. The absorbent structure may be used in any product utilized to absorb and retain a fluid including surface wipes. The absorbent structure may be used as a paper towel. Exemplary absorbent articles in the context of the present invention are disposable absorbent articles.

The absorbent structures single stratum may be a heterogeneous mass comprising enrobeable elements and one or more portions of foam pieces. The discrete portions of foam pieces are open-celled foam. The foam may be a High Internal Phase Emulsion (HIPE) foam.

The absorbent structure single stratum may be an absorbent core for an absorbent article wherein the absorbent core comprises a heterogeneous mass comprising fibers and one or more discrete portions of foam that are immobilized in the heterogeneous mass or may be combined with other layers to form an absorbent core. Other layers may contain liquid absorbent materials suitable for use in an absorbent core. Nonlimiting examples of liquid-absorbent materials suitable for use in or as a layer of an absorbent core may include comminuted wood pulp which is generally referred to as airfelt; creped cellulose wadding; absorbent gelling materials including superabsorbent polymers such as hydrogel-forming polymeric gelling agents; chemically stiffened, modified, or cross-linked cellulose fibers; meltblown polymers including coform; synthetic fibers including crimped polyester fibers; tissue including tissue wraps and tissue laminates; capillary channel fibers; absorbent foams; absorbent sponges; synthetic staple fibers; peat moss; or any equivalent material; or combinations thereof, as is well known in the art of making catamenial products such as sanitary napkins, pantiliners, incontinence pads, and the like.

In the following description of the invention, the surface of the article, or of each component thereof, which in use faces in the direction of the wearer is called wearer-facing surface. Conversely, the surface facing in use in the direction of the garment is called garment-facing surface. The absorbent article of the present invention, as well as any element thereof, such as, for example the absorbent core, has therefore a wearer-facing surface and a garment-facing surface.

The present invention relates to an absorbent structure single stratum that contains one or more discrete open-cell foam pieces foams that are integrated into a heterogeneous mass comprising one or more enrobeable elements integrated into the one or more open-cell foams such that the two may be intertwined.

The open-cell foam pieces may comprise between 1% of the heterogeneous mass by volume to 99% of the heterogeneous mass by volume, such as, for example, 5% by volume, 10% by volume, 15% by volume, 20% by volume, 25% by volume, 30% by volume, 35% by volume, 40% by volume, 45% by volume, 50% by volume, 55% by volume, 60% by volume, 65% by volume, 70% by volume, 75% by volume, 80% by volume, 85% by volume, 90% by volume, or 95% by volume.

The heterogeneous mass may have void space found between the enrobeable elements, between the enrobeable elements and the enrobed elements, and between enrobed elements. The void space may contain a gas such as air. The void space may represent between 1% and 95% of the total volume for a fixed amount of volume of the heterogeneous mass, such as, for example, 5%, 10%, 15%, 20%, 25%, 30%, 35%, 40%, 45%, 50%, 55%, 60%, 65%, 70%, 75%, 80%, 85%, 90% of the total volume for a fixed amount of volume of the heterogeneous mass.

The combination of open-cell foam pieces and void space within the heterogeneous mass may exhibit an absorbency of between 10 g/g to 200 g/g of the, such as for example, between 20 g/g and 190 g/g of the heterogeneous mass, such as, for example 30 g/g, 40 g/g, 60 g/g, 80 g/g, 100 g/g, 120 g/g, 140 g/g 160 g/g 180 g/g or 190 g/g of the heterogeneous mass. Absorbency may be quantified according to the EDANA Nonwoven Absorption method 10.4-02.

The open-cell foam pieces are discrete foam pieces intertwined within and throughout a heterogeneous mass such that the open-cell foam enrobes one or more of the enrobeable elements such as, for example, fibers within the mass. The open-cell foam may be polymerized around the enrobeable elements.

A discrete open-cell foam piece may enrobe more than one enrobeable element. The enrobeable elements may be enrobed together as a bunch or bundle. Alternatively, more than one enrobeable element may be enrobed by the discrete open-cell foam piece without contacting another enrobeable element.

A discrete open-cell foam piece may be immobilized such that the discrete open-cell foam piece does not change location within the heterogeneous mass during use of the absorbent structure.

The open-cell foam pieces may be discrete. Open-cell foam pieces are considered discrete in that they are not continuous throughout the entire heterogeneous mass. Not continuous throughout the entire heterogeneous mass represents that at any given point in the heterogeneous mass, the open-cell absorbent foam is not continuous in at least one of the cross sections of a longitudinal, a vertical, and a lateral plane of the heterogeneous mass. The absorbent foam may or may not be continuous in the lateral and the vertical planes of the cross section for a given point in the heterogeneous mass. The absorbent foam may or may not be continuous in the longitudinal and the vertical planes of the cross section for a given point in the heterogeneous mass. The absorbent foam may or may not be continuous in the longitudinal and the lateral planes of the cross section for a given point in the heterogeneous mass.

When the open-cell foam is not continuous in at least one of the cross sections of the longitudinal, the vertical, and the lateral plane of the heterogeneous mass, one or both of either the enrobeable elements or the open-cell foam pieces may be bi-continuous throughout the heterogeneous mass.

The open-cell foam pieces may be located at any point in the heterogeneous mass. A foam piece may be surrounded by the elements that make up the enrobeable elements. A foam piece may be located on the outer perimeter of the heterogeneous mass such that only a portion of the foam piece is entangled with the elements of the heterogeneous mass.

The open-cell foam pieces may expand upon being contacted by a fluid to form a channel of discrete open-cell foam pieces. The open-cell foam pieces may or may not be in contact prior to being expanded by a fluid.

The open cell foam pieces may be impregnated prior to polymerization into or onto two or more different enrobeable elements that are combined to create a heterogeneous mixture of enrobeable elements. The two or more different enrobeable elements may be intertwined such that one enrobeable element may be surrounded by multiples of the second enrobeable element, such as, for example by using more than one type of fiber in a mixture of fibers or by coating one or more fibers with surfactant. The two or more different enrobeable elements may be layered within the heterogeneous mass along any of the vertical, longitudinal, and/or lateral planes such that the enrobeable elements are profiled within the heterogeneous mass for an enrobeable element inherent property or physical property, such as, for example, hydrophobicity, fiber diameter, fiber or composition. It is understood that any inherent property or physical property of the enrobeable elements listed is contemplated herein.

After being impregnated into or onto the enrobeable elements, the open-celled foam in either a liquid or solid state are polymerized to form one or more open-cell foam pieces. The open-celled foam may be polymerized using any known method including, for example, heat, UV, and infrared. Following the polymerization of a water in oil open-cell foam emulsion, the resulting open-cell foam is saturated with aqueous phase that needs to be removed to obtain a substantially dry open-cell foam. Removal of the saturated aqueous phase or dewatering may occur using nip rollers, and vacuum. Utilizing a nip roller may also reduce the thickness of the heterogeneous mass such that the heterogeneous mass will remain thin until the open-cell foam pieces entwined in the heterogeneous mass are exposed to fluid.

The open-cell foam pieces may enrobe the enrobeable elements in a manner that creates a spacing or vacuole between the enrobing foam and the enrobeable element. As described herein, a vacuole is a spacing or gap between a portion of an enrobeable element and the open-cell foam that contains at least a portion of the enrobeable element. As described herein, a vacuole is not formed when the cross sectional perimeter of the enrobeable element is in full contact with the open cell foam or wherein the open cell foam is connected to the enrobeable element by cell walls that are attached to at least 40% of the cross sectional perimeter of the enrobeable element. In a case of two or more bundled fibers, a vacuole may be created by the spacing formed by the two or more fibers such that the open cell foam is not in contact with the entire outer perimeter of any one of the two or more bundled fibers.

The vacuole contains the enrobeable element and may surround the entire element, a cross section of the element, or a portion of the element. In an embodiment, the open-cell foam pieces may be in direct contact with the element at one location and spaced by a vacuole in another. The vacuole may allow the enrobeable element to move within the vacuole. The size of the vacuole may be driven by the type of enrobeable element. In an embodiment, the vacuole diameter is greater than the fiber diameter which is greater than the foam pore size. The vacuole diameter may be, for example, between 1.001 and 30,000 times the diameter of the fiber diameter, such as, between 1.2 and 20,000 times the diameter of the fiber, between 1 and 10 times the diameter of the fiber, between 10 and 10,000 times the diameter of the fiber, between 100 and 1,000 times the diameter of the fiber, such as, for example, 20 times the diameter of the fiber, 150 times the diameter of the fiber, 1,500 times the diameter of the fiber, 3,000 times the diameter of the fiber, 4,500 times the diameter of the fiber, 6,000 times the diameter of the fiber, 7,500 times the diameter of the fiber, 9,000 times the diameter of the fiber, 12,000 times the diameter of the fiber, 15,000 times the diameter of the fiber, 18,000 times the diameter of the fiber, 21,000 times the diameter of the fiber, 24,000 times the diameter of the fiber, 27,000, or 29,000 times the diameter of the fiber.

In an embodiment, one or more vacuoles may be irregularly shaped. In such embodiments, the cross-sectional surface area of the vacuoles may be between 1.0002 and 900,000,000 times the surface area created by a cross section of the fiber. When more than one fiber is located in the same vacuole, the cross-sectional surface area of the vacuoles may be between 1.0002 and 900,000,000 times the surface area created by the sum of the cross section of the fibers, such as, for example, between 10 to 100,000,000 times the surface area created by the sum of the cross section of the fibers, between 1,000 to 1,000,000 times the surface area created by the sum of the cross section of the fibers, or between 10,000 to 100,000 times the surface area created by the sum of the cross section of the fibers.

In an embodiment, the cross-sectional surface area of the vacuoles may be between 1.26 and 9,000,000 times the cross-sectional surface area of the pores in the open-cell foam such as, for example between 100 and 5,000,000 times the cross-sectional surface area of the pores in the open-cell foam, between 1,000 and 1,000,000 times the cross-sectional surface area of the pores in the open-cell foam, between 100,000 and 500,000 times the cross-sectional surface area of the pores in the open-cell foam. The cross sectional area of the pores may be between 0.001% and 99.99% of the cross sectional area of the vacuoles. The cross-sectional surface area of the vacuoles, pores (also referred to as cells) of the open-cell foams, and fiber diameters are measured via quantitative image analysis of cross-sectional micrographs of the heterogeneous mass.

Dependent upon the desired foam density, polymer composition, specific surface area, or pore size (also referred to as cell size), the open-celled foam may be made with different chemical composition, physical properties, or both. For instance, dependent upon the chemical composition, an open-celled foam may have a density of 0.0010 g/cc to about 0.25 g/cc. Preferred 0.04 g/cc.

Open-cell foam pore sizes may range in average diameter of from 1 to 800 μm, such as, for example, between 50 and 700 μm, between 100 and 600 μm, between 200 and 500 μm, between 300 and 400 μm.

In some embodiments, the foam pieces have a relatively uniform cell size. For example, the average cell size on one major surface may be about the same or vary by no greater than 10% as compared to the opposing major surface. In other embodiments, the average cell size of one major surface of the foam may differ from the opposing surface. For example, in the foaming of a thermosetting material it is not uncommon for a portion of the cells at the bottom of the cell structure to collapse resulting in a lower average cell size on one surface.

Without being bound by theory, it has been found that one can manipulate the vacuole size within the heterogeneous mass by changing the enrobeable elements exterior properties, bundling one or more enrobeable elements, choosing different enrobeable elements, adding a surfactant to the exterior of the enrobeable element, the concentration of a surfactant placed on the enrobeable element, and combinations thereof. Different surfactant systems which may be placed on the enrobeable elements before the emulsion is placed on the elements include ionic surfactants, such as, for example, zwitterionic surfactants, derivatized polysiloxane surfactants, anionic surfactants, cationic surfactants, or combinations thereof. Specifically, it has been found that one can treat a naturally hydrophilic fiber (i.e. rayon) with a nonionic surfactant to reduce or eliminate vacuole formation and with an ionic surfactant to increase or create a vacuole size. Additionally, it has been found that vacuole size may be changed based on the enrobeable element material chosen due to its external surface properties, such as, for example, the vacuole size created by enrobing rayon fibers with open-cell foam is different than the vacuole size created by enrobing polypropylene fibers. Additionally, one may bundle a set of fibers that, individually would not create a vacuole, to create a vacuole among or enrobing the bundle of fibers.

Polysiloxane Surfactants
Polyalkyleneoxide polysiloxane compounds, especially those having a molecular weight of less than about 1,000, greatly enhance the ability of a composition to distribute (or spread) across a surface treated with the composition. Also, it has been found that such compounds, when used in compositions for treating fabrics, greatly enhance the ability of the composition to penetrate in between fibers of fabrics. However, such polyalkyleneoxide polysiloxane surfactants can be rather unstable in aqueous compositions. It has been found that the pH of the present compositions needs to be carefully controlled and thus the present compositions require a suitable buffering agent to stabilize these compositions comprising relatively low molecular weight polyalkyleneoxide polysiloxane surfactants. The polysiloxane surfactants may also contain amino silicone or cationic silicone groups.

The polyalkyleneoxide polysiloxane surfactants suitable in the stable, aqueous compositions of the present invention have the general formula:

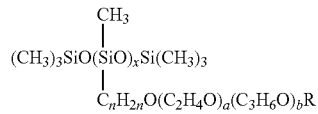

wherein
x has a value of from about 1 to about 8; preferably from about 1 to 3; and more preferably 1;
n has a value of from about 3 to about 4, preferably n is about 3;
a has a value of from about 1 to about 15, preferably a is from about 6 to about 10;
b has a value of from about 0 to about 14, preferably b is from about 0 to about 3: and most preferably b is about 0,
a+b has a value of from about 5 to about 15, preferably from about 6 to about 10 and
R is selected from the group consisting of hydrogen, an alkyl group having from about 1 to about 4 carbon atoms, and an acetyl group.

Cationic Surfactants
Cationic surfactants suitable for coating an enrobeable element include but are not limited to those surfactants that contain cationic functional groups at their head, such as alkyl ammonium chlorides, trimethylalkylammonium chlorides, and the chlorides or bromides of benzalkonium and alkylpyridinium ions. Cationic surfactants include but are not limited to dodecyltrimethylammonium bromide (DTAB), and carboshield 1000 cationic.

Cationic surfactants can increase the ability of a composition to spread across surfaces, such as nonwoven fabrics. Such cationic surfactants also improve the ability of the present compositions to penetrate in between the fibers of nonwoven fabrics.

Cationic surfactants useful herein are preferably selected from the group consisting of quaternary ammonium compounds, biguanide compounds, and mixtures thereof.

Quaternary Compounds
A wide range of quaternary compounds can be used as cationic surfactants herein. Non-limiting examples of useful quaternary compounds include: (1) benzalkonium chlorides and/or substituted benzalkonium chlorides such as commercially available Barquat® (available from Lonza), Maquat® (available from Mason), Variquat® (available from Witco/Sherex), and Hyamine® (available from Lonza); (2) di(C6-C14)alkyl di short chain (C1-4 alkyl and/or hydroxyalkl) quaternary such as Bardac® products of Lonza, (3) N-(3-chloroallyl) hexaminium chlorides such as Dowicide® and Dowicil® available from Dow: (4) benzethonium chloride such as Hyamine® from Rohm & Haas; (5) methylbenzethonium chloride represented by Hyamine® 10* supplied by Rohm & Haas, (6) cetylpyridinium chloride such as Cepacol chloride available from of Merrell Labs. Examples of dialkylquaternary compounds include di(C8-C12)dialkyl dimethyl ammonium chloride, such as didecyldimethylammonium chloride (Bardac 22), dioctyidimethylammonium chloride (Bardac 2050), other dialkyldimethylammonium chlorides, alkyldimethylbenzylammonium chlorides, dialkylmethylbenzylammonium chlorides, and mixtures thereof. Other cationic surfactants include diisobutylphenoxyethoxyethyl dimethylbenzylammonium chloride (commercially available under the trade name Hyamine® 1622 from Rohm & Haas) and (methyl)diisobutylphenoxyethoxyethyl dimethylbenzylammonium chloride (i.e. methylbenzethonium chloride).

Biguanide Compounds

Other useful cationic surfactants herein include biguanide compounds. As with the quaternary compounds described hereinbefore, many biguanide compounds exhibit antimicrobial effectiveness, depending on the level of the biguanide compound in the compositions. Especially useful biguanide compounds include 1,1'-hexamethylene bis(5-(p-chlorophenyl)biguanide), commonly known as chlorhexidine, and its salts, e.g., with hydrochloric, acetic and gluconic acids. Other useful biguanide compounds include Cosmocil® CQ®, Vantocil® IB, including poly (hexamethylene biguanide) hydrochloride. Other useful cationic surfactants include the bis-biguanide alkanes.

Suitable counterions associated with cationic surfactants include; chloride, bromide, methylsulfate, ethylsulfate, phenylsulfonates such as p-methylphenyl sulfonates, nitrates, acetates, gluconates, sulfate, and nitrate, more preferably chloride and methyl sulfate. The anion can also, but less preferably, carry a double charge in which case A- represents half a group.

Nonionic Surfactants

Suitable nonionic surfactants include, but are not limited to, alkyl ethoxylated surfactants, block copolymer surfactants, castor oil surfactants, sorbitan ester surfactants, polyethoxylated fatty alcohol surfactants, glycerol mono-fatty acid ester surfactants, polyethylene glycol fatty acid ester surfactants, and mixtures thereof.

Alkyl Ethoxylated Surfactants

A nonlimiting type of nonionic surfactant is alkyl ethoxylated surfactant, such as addition products of ethylene oxide with fatty alcohols, fatty acids, fatty amines, etc. Optionally, addition products of mixtures of ethylene oxide and propylene oxide with fatty alcohols, fatty acids, fatty amines can be used. The ethoxylated surfactant includes compounds having the general formula:

$$R^8—Z—(CH_2CH_2O)_sB$$

wherein R8 is an alkyl group or an alkyl aryl group, selected from the group consisting of: primary, secondary and branched chain alkyl hydrocarbyl groups, primary, secondary and branched chain alkenyl hydrocarbyl groups, and/or primary, secondary and branched chain alkyl- and alkenyl-substituted phenolic hydrocarbyl groups having from about 6 to about 20 carbon atoms, preferably from about 8 to about 18, more preferably from about 10 to about 15 carbon atoms; s is an integer from about 2 to about 45, preferably from about 2 to about 20, more preferably from about 2 to about 15; B is hydrogen, a carboxylate group, or a sulfate group; and linking group Z is selected from the group consisting of: —O—, —N(R)x—, —C(O)O—, —C(O)N(R)—, —C(O)N(R)—, and mixtures thereof, in which R, when present, is $R^8$, a lower alkyl with about 1 to about 4 carbons, a polyalkylene oxide, or hydrogen, and x is 1 or 2.

The nonionic alkyl ethoxylated surfactants herein are characterized by an HLB (hydrophilic-lipophilic balance) of from about 5 to about 20, preferably from about 6 to about 15.

Block Copolymer Surfactants

Nonlimiting examples of nonionic surfactants include block copolymers of ethylene oxide and propylene oxide. Suitable block polyoxyethylene-polyoxypropylene polymeric surfactants, that are compatible with most cyclodextrins, include those based on ethylene glycol, propylene glycol, glycerol, trimethylolpropane and ethylenediamine as the initial reactive hydrogen compound. Polymeric compounds made from a sequential ethoxylation and propoxylation of initial compounds with a single reactive hydrogen atom, such as C12-18 aliphatic alcohols, are not generally compatible with the cyclodextrin. Certain of the block polymer surfactant compounds designated Pluronic® and Tetronic® by the BASF-Wyandotte Corp., Wyandotte, Mich., are readily available.

Sorbitan Ester Surfactants

The sorbitan esters of long-chain fatty acids usable surfactants include those having long-chain fatty acid residues with 14 to 26 carbon atoms, desirably 16 to 22 carbon atoms. Furthermore, the esterification degree of the sorbitan polyesters of long-chain fatty acids is desirably 2.5 to 3.5, especially 2.8 to 3.2. Typical examples of these sorbitan polyesters of long-chain fatty acids are sorbitan tripalmitate, sorbitan trioleate, and sorbitan tallow fatty acid triesters.

Anionic Surfactants

Anionic surfactants suitable for coating an enrobeable element include but are not limited to those surfactants that contain anionic functional groups at their head, such as sulfate, sulfonate, phosphate, and coarbxylates. Many suitable nonlimiting examples from the class of anionic surfactants can be found in Surfactants and Interfacial Phenomena, 2nd Ed., Milton J. Rosen, 1989, John Wiley & Sons, Inc., pp. 7-16, which is hereby incorporated by reference. Additional suitable nonlimiting examples of anionic surfactants can be found in Handbook of Surfactants, M. R. Porter, 1991, Blackie & Son Ltd, pp. 54-115 and references therein, the disclosure of which is incorporated herein by reference.

Structurally, suitable anionic surfactants contain at least one hydrophobic moiety and at least one hydrophilic moiety. The surfactant can contain multiple hydrophobic moieties and/or multiple hydrophilic moieties, but preferably less than or equal to about 2 hydrophobic moieties and less than or equal to about 3 hydrophilic moieties. The hydrophobic moiety is typically comprised of hydrocarbons either as an alkyl group or an alkyl-aryl group. Alkyl groups typically contain from about 6 to about 22 carbons, preferably about 10 to about 18 carbons, and more preferably from about 12 to about 16 carbons, aryl groups typically contain alkyl groups containing from about 4 to about 6 carbons. Each alkyl group can be a branched or linear chain and is either saturated or unsaturated. A typical aryl group is benzene. Some typical hydrophilic groups for anionic surfactants include but are not limited to —CO2-, —OSO3-, —SO3-, —(OR1)x —CO2-, —(OR1)x —OSO3-, —(OR1)x —SO3- where x is being less than about 10 and preferably less than about 5. Some nonlimiting examples of suitable surfactants includes, Stepanol® WAC, Biosoft® 40 (Stepan Co., Northfield, Ill.). Other examples of Anionic surfactants include but are not limited to Sodium dodecylbenzene sulfonate (SDBS), ammonium lauryl sulfate, Sodium Lauryl Sulfate or Sodium Dodecyl sulfate (SDS), alkyl-ether sulfates sodium laureth sulfate, and sodium myreth sulfate.

Anionic surfactants can also be created by sulfating or sulfonating animal or vegetable based oils. An example of these type of surfactants include sulfated canola oil and sulfated castor oil (Freedom SCO-75) available from the Freedom Chemical Co., Charlotte N.C. (owned by BF Goodrich).

Nonlimiting examples of cyclodextrin-compatible anionic surfactants are the alkyldiphenyl oxide disulfonate, having the general formula: (Chemical Structure image '18' not included in text) wherein R is an alkyl group. Examples of this type of surfactants are available from the Dow Chemical Company under the trade name Dowfax® wherein R is a linear or branched C6-C16 alkyl group. An example of these cyclodextrin-compatible anionic surfactant is Dowfax 3B2 with R being approximately a linear C10 group.

Zwitterionic Surfactants

Zwitterionics are suitable for use in the present invention. Zwitterionic surfactants, also referred to as amphoteric surfactants, comprise moieties that can have both negative and positive charges. Zwitterionics have advantages over other surfactants since these are less irritating to the skin and yet still provide good wetting. Some nonlimiting examples of zwitterionic surfactants useful for the present invention are: betaines, amine-oxides, sulfobetaines, sultaines, glycinates, aminoipropionates, imidazoline-based amphoterics. Various zwitterionic surfactants are disclosed in the "Handbook of Surfactants" by M. R. Porter, Chapman & Hall, 1991 and references therein and in "Surfactants and Interfacial Phenomena" by M. Rosen, 2nd Ed., John Wiley & Sons. 1989 and references therein, which are incorporated herein by reference. Zwitterionics disclosed in the "Handbook of Surfactants" and in "Surfactants and Interfacial Phenomena" and references therein are incorporated herein by reference.

Fluorocarbon Surfactants

Fluorocarbon surfactants are a class of surfactants wherein the hydrophobic part of the amphiphile comprises at least in part some portion of a carbon-based linear or cyclic moiety having fluorines attached to the carbon where typically hydrogens would be attached to the carbons together with a hydrophilic head group. Some typical nonlimiting fluorocarbon surfactants include fluorinated alkyl polyoxyalkylene, and fluorinated alkyl esters as well as ionic surfactants.

Without being bound by theory, Applicants have found that hydrophobic surfactants or enrobeable elements lead to minor vacuole or no vacuole formation while hydrophilic surfactants or enrobeable elements lead to larger vacuole formation. This allows for the manipulation of vacuole size within the same structure and using the same emulsion by combining one or more enrobeable elements that exhibit different hydrophobic/hydrophilic properties based on either the material chosen or the surfactant used to treat the enrobeable element.

FIGS. 1 to 8 are SEM micrographs of a portion of a stratum 24 containing HIPE foam pieces 20 intertwined within a heterogeneous mass 18 comprising enrobeable elements 30 in the form of different nonwoven fibers 22. As shown in FIGS. 1-8, the vacuole size surrounding a fiber can be manipulated by coating enrobeable elements in the form of fibers with different surfactants. Additionally, one may control the size of the vacuoles by selecting fibers that have specific surface properties or by grouping fibers in a bundle. As shown in FIGS. 2-8, the open-cell HIPE foam pieces 20 comprise pores 26.

FIG. 1 shows an SEM micrograph of a heterogeneous mass 18 taken at a magnification of 150×. As shown in FIG. 1, the HIPE foam piece 20 enrobes a portion of one or more fiber 22 such that the fibers bisect through the HIPE foam piece 20. The HIPE foam piece 20 enrobe the fibers such that the pieces are not free to move about within the stratum 24. The fibers 22 of FIG. 1 are phobic and have a non-ionic coating. As shown in FIG. 1, the fibers are enrobed without vacuoles.

Figure 2:
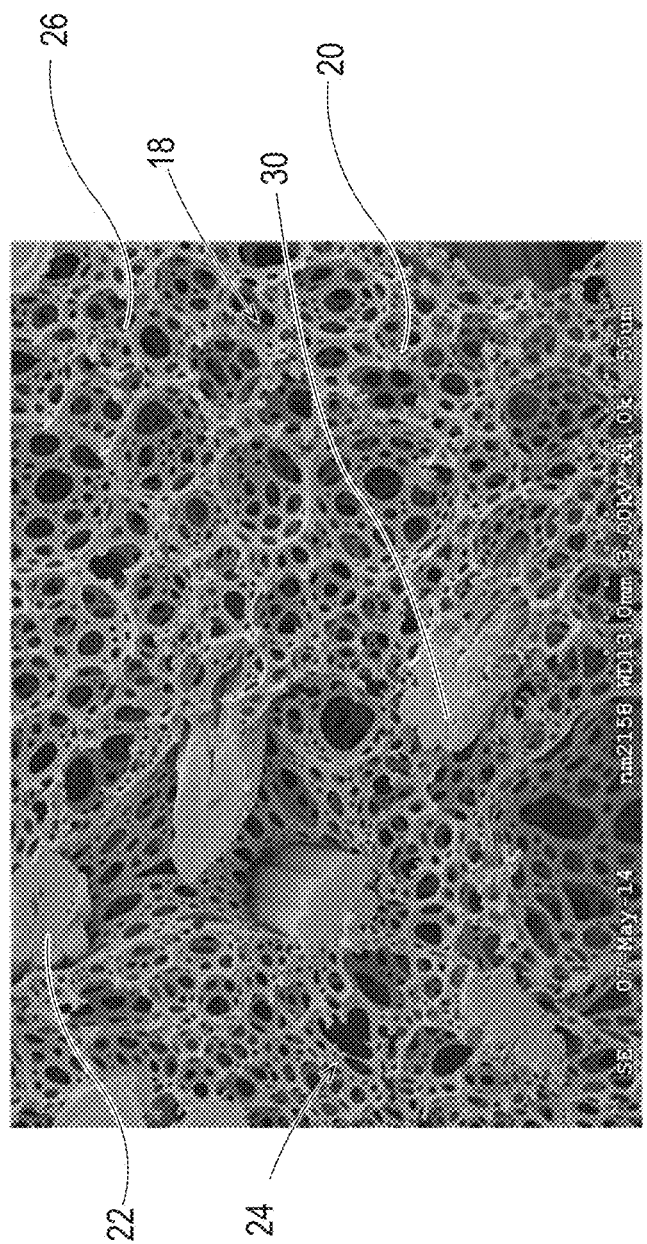
FIG. 2 is an SEM of a representative HIPE foam piece enrobing one or more fibers.

FIG. 2 shows an SEM micrograph of a heterogeneous mass 18 taken at a magnification of 1,000×. As shown in FIG. 2, the HIPE foam piece 20 enrobes a portion of one or more fiber 22 such that the fibers bisect through the HIPE foam piece 20. The HIPE foam piece 20 enrobe the fibers such that the pieces are not free to move about within the stratum 24. The fibers 22 of FIG. 2 are phobic and have a non-ionic coating. As shown in FIG. 1, the fibers are enrobed without vacuoles.

Figure 3:
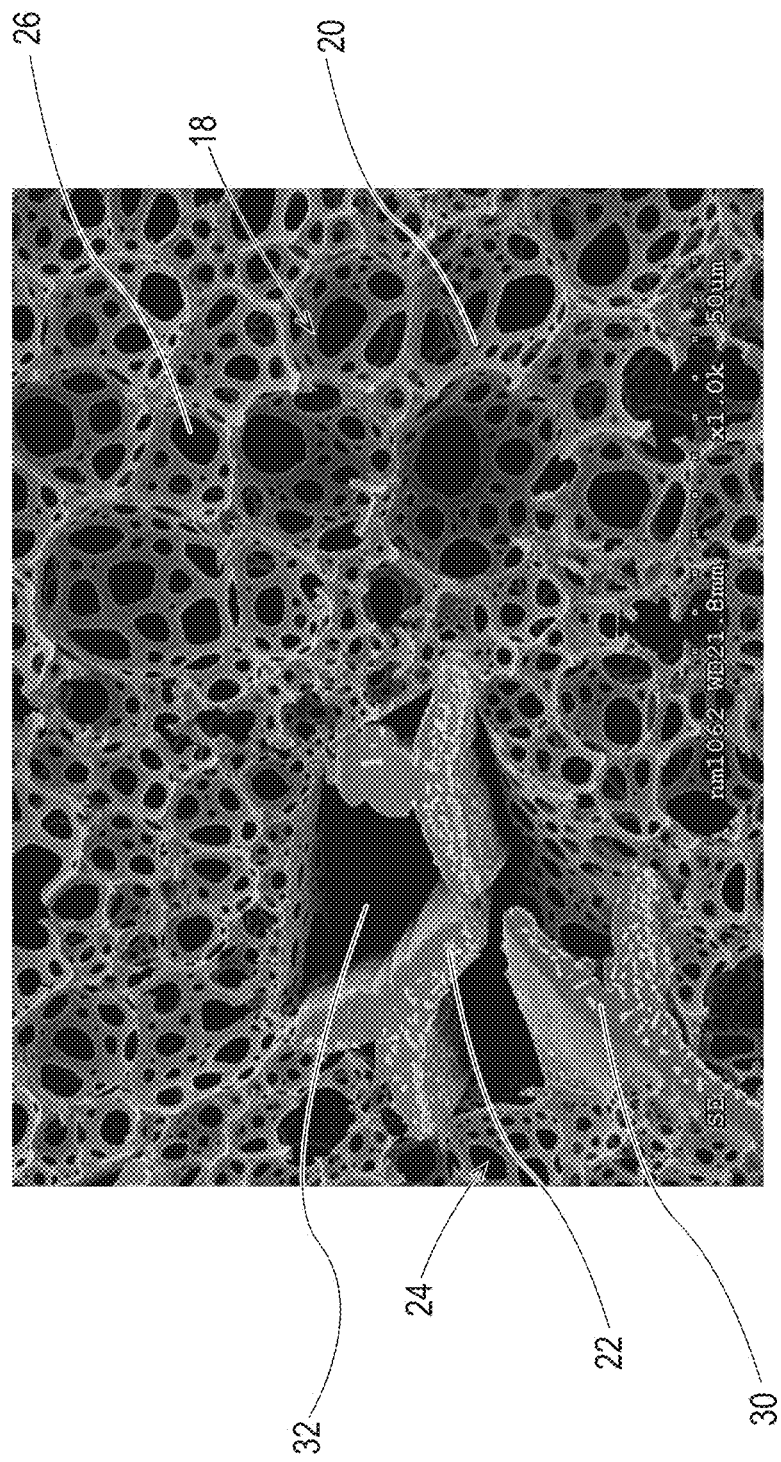
FIG. 3 is an SEM of a representative HIPE foam piece enrobing one or more fibers.

FIG. 3 shows an SEM micrograph of a heterogeneous mass 18 taken at a magnification of 1,000×. As shown in FIG. 3, the HIPE foam piece 20 enrobes a portion of one or more fiber 22 such that the fibers bisect through the HIPE foam piece 20. The HIPE foam piece 20 enrobe the fibers such that the pieces are not free to move about within the stratum 24. The fibers shown in FIG. 3 are trilobal and bundled together. As shown in FIG. 3, a vacuole 32 is formed due to the bundled geometric shape of the fiber.

Figure 4:
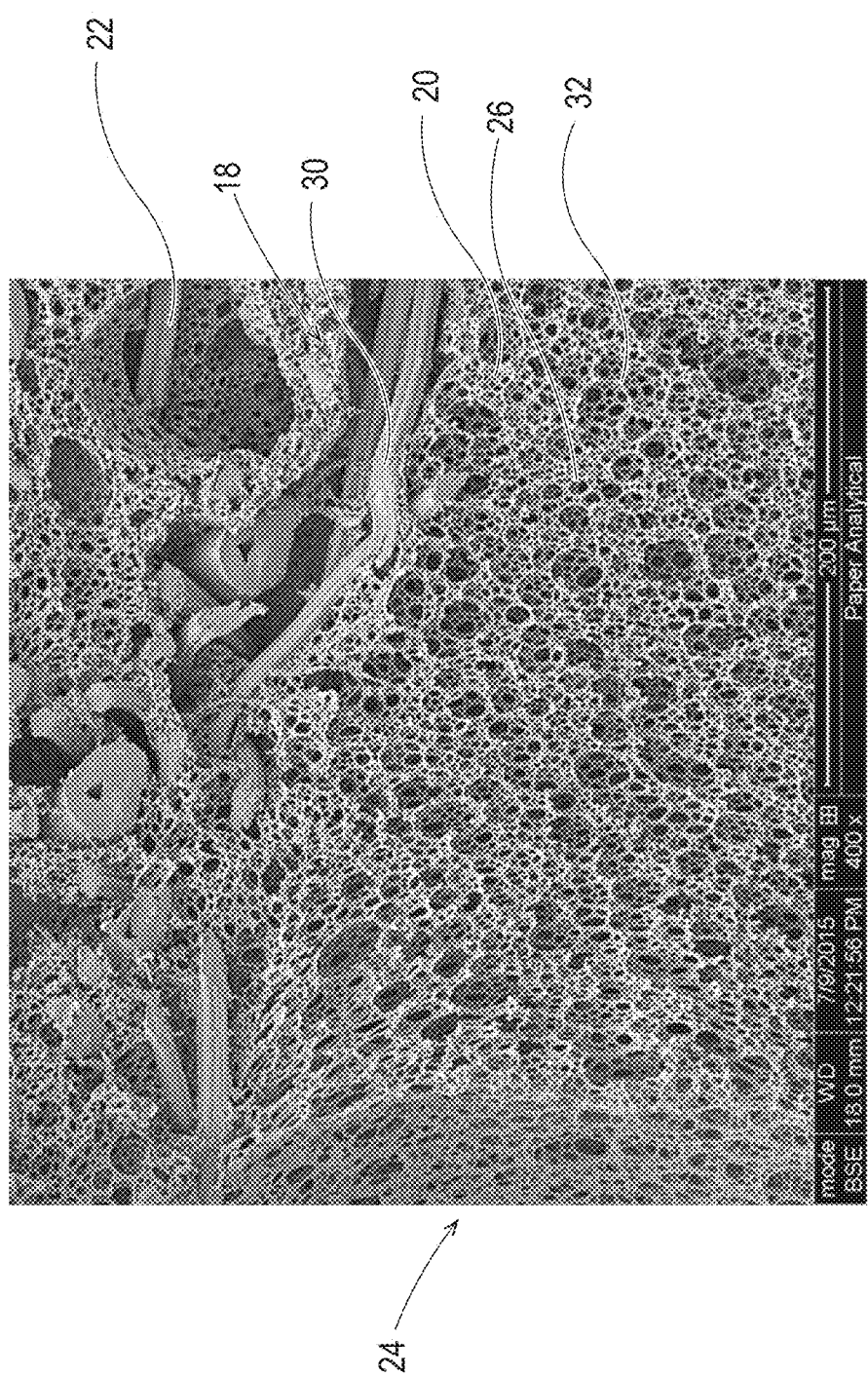
FIG. 4 is an SEM of a representative HIPE foam piece enrobing one or more fibers.

FIG. 4 shows an SEM micrograph of a heterogeneous mass 18 taken at a magnification of 400×. As shown in FIG. 4, the HIPE foam piece 20 enrobes a portion of one or more fiber 22 such that the fibers bisect through the HIPE foam piece 20. The HIPE foam piece 20 enrobe the fibers such that the pieces are not free to move about within the stratum 24. The fibers 22 of FIG. 4 comprise rayon that has been stripped of any hydrophobic coating. As shown in FIG. 4, a vacuole 32 is formed due to the surface property of the fiber.

Figure 5:
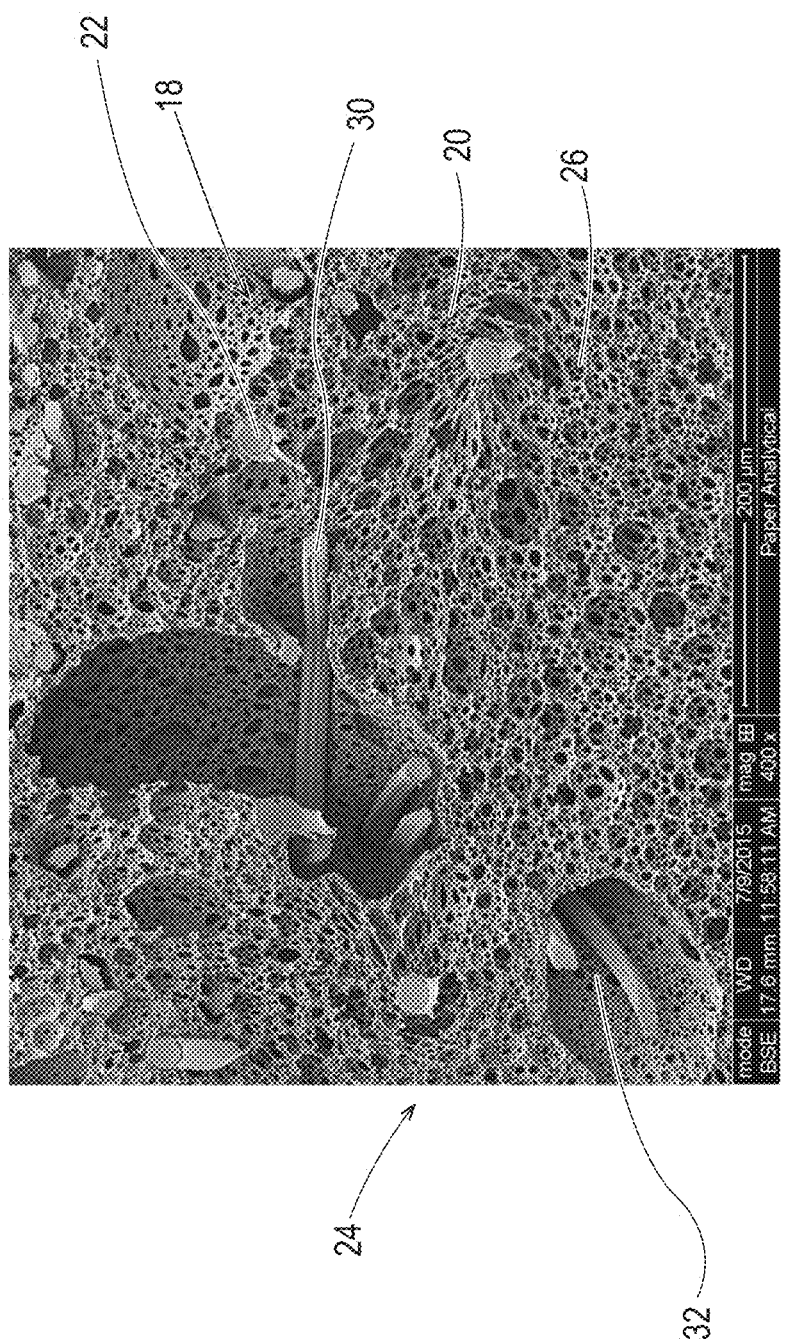
FIG. 5 is an SEM of a representative HIPE foam piece enrobing one or more fibers.

FIG. 5 shows an SEM micrograph of a heterogeneous mass 18 taken at a magnification of 400×. As shown in FIG. 5, the HIPE foam piece 20 enrobes a portion of one or more fiber 22 such that the fibers bisect through the HIPE foam piece 20. The HIPE foam piece 20 enrobe the fibers such that the pieces are not free to move about within the stratum 24. A portion of the fibers 22 of FIG. 5 have been treated with an anionic surfactant. As shown in FIG. 5, a vacuole 32 is formed due to the anionic surfactant coating on the fibers.

Figure 6:
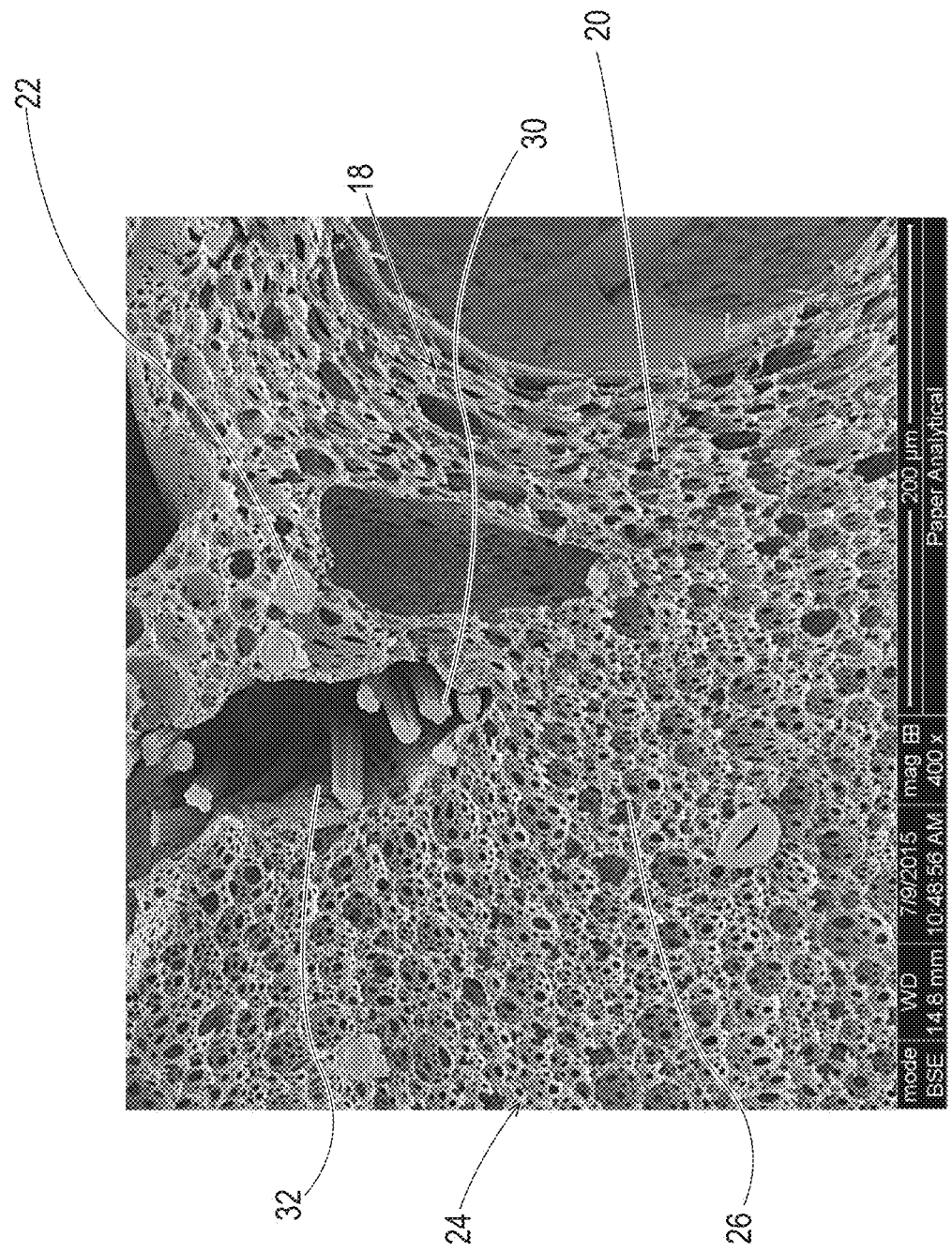
FIG. 6 is an SEM of a representative HIPE foam piece enrobing one or more fibers.

FIG. 6 shows an SEM micrograph of a heterogeneous mass 18 taken at a magnification of 400×. As shown in FIG. 6, the HIPE foam piece 20 enrobes a portion of one or more fiber 22 such that the fibers bisect through the HIPE foam piece 20. The HIPE foam piece 20 enrobe the fibers such that the pieces are not free to move about within the stratum 24. A portion of the fibers 22 of FIG. 6 have been treated with an cationic surfactant. As shown in FIG. 6, a vacuole 32 is formed due to the cationic surfactant coating on the fibers.

Figure 7:
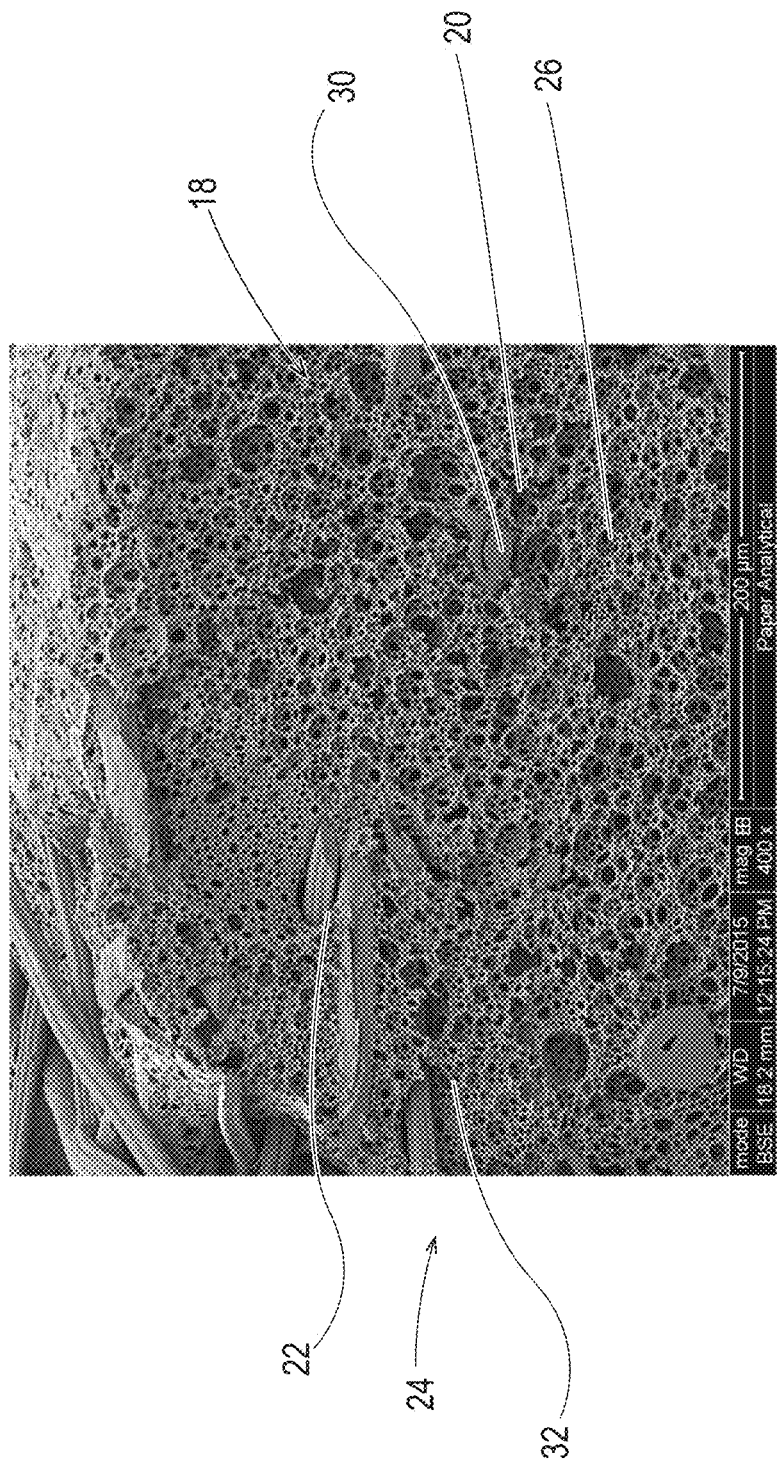
FIG. 7 is an SEM of a representative HIPE foam piece enrobing one or more fibers.

FIG. 7 shows an SEM micrograph of a heterogeneous mass 18 taken at a magnification of 400×. As shown in FIG. 7, the HIPE foam piece 20 enrobes a portion of one or more fiber 22 such that the fibers bisect through the HIPE foam piece 20. The HIPE foam piece 20 enrobe the fibers such that the pieces are not free to move about within the stratum 24. The fibers 22 of FIG. 7 are hydrophobic due to the addition of a nonionic surfactant. As shown in FIG. 7, the open-cell foam enrobes the hydrophobic fibers without the presence of vacuoles.

Figure 8:
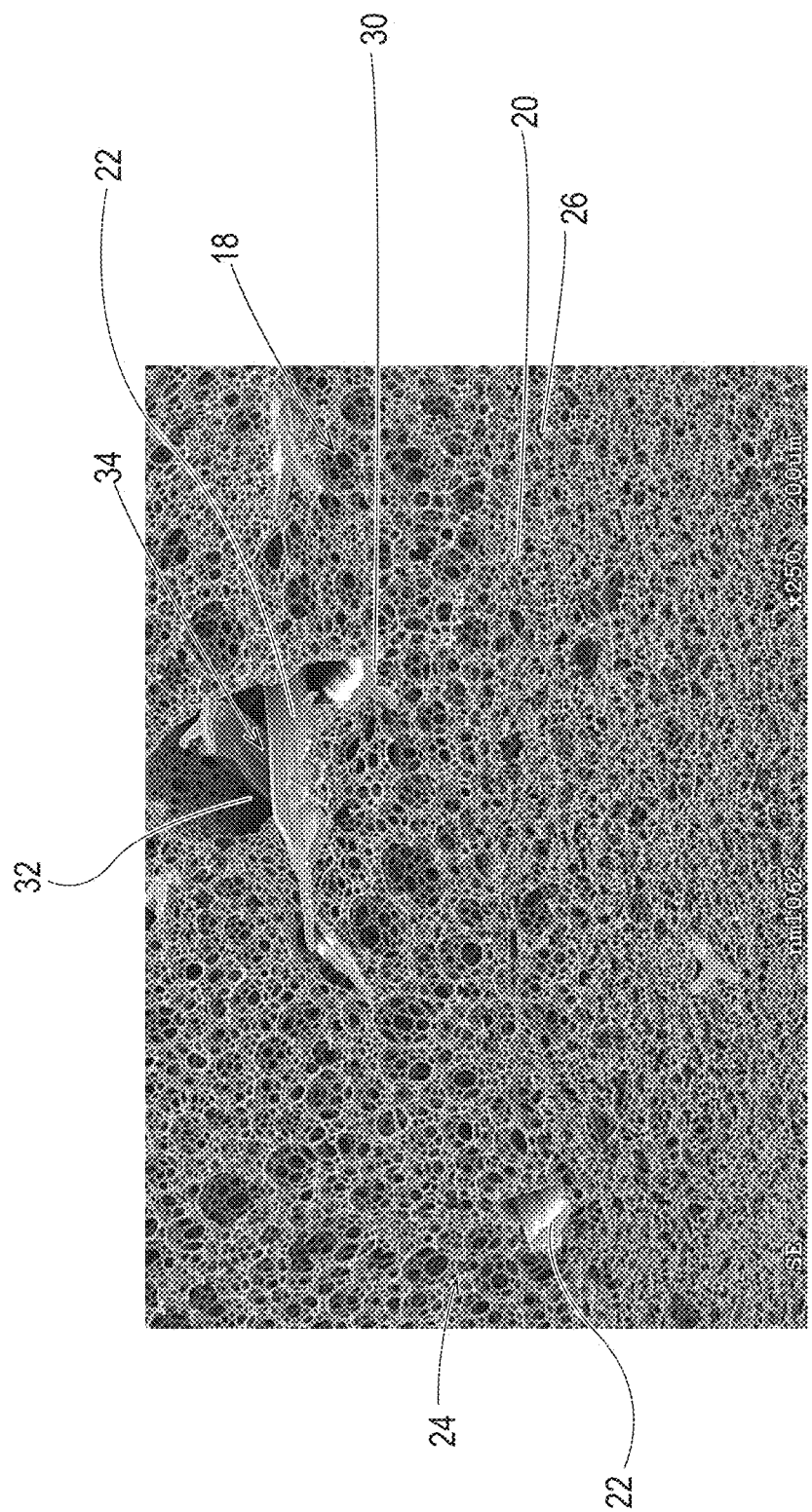
FIG. 8 is an SEM of a representative HIPE foam piece enrobing one or more fibers.

FIG. 8 shows an SEM micrograph of a heterogeneous mass 18 taken at a magnification of 250×. As shown in FIG. 1, the HIPE foam piece 20 enrobes a portion of one or more fiber 22 such that the fibers bisect through the HIPE foam piece 20. The HIPE foam piece 20 enrobe the fibers such that the pieces are not free to move about within the stratum 24. The fibers 22 of FIG. 8 are all treated with a nonionic surfactant. The fiber 22 in FIG. 8 are trilobal in shape. As shown in FIG. 8, the bundled fibers comprise a vacuole 32 while the other trilobal fibers are enrobed without the presence of a vacuole.

Figure 9:
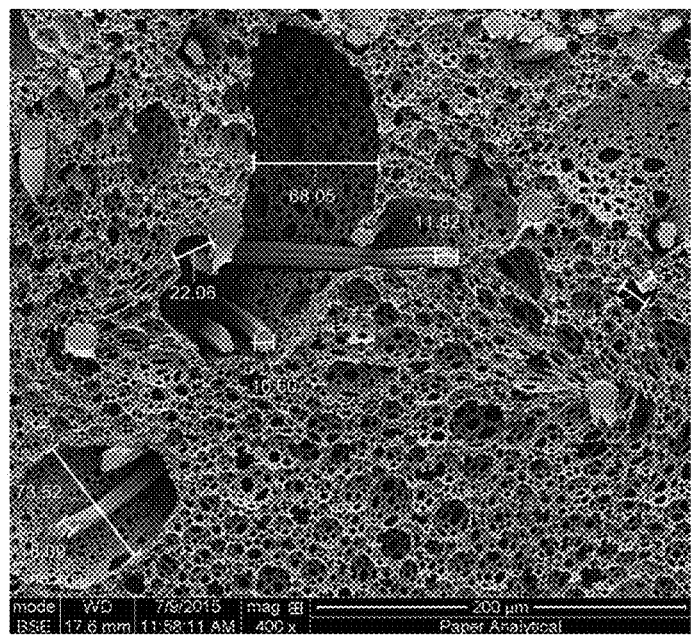
FIG. 9 is the SEM of FIG. 5 including measurements.

FIG. 9 shows the SEM of FIG. 5 with measurements on both fibers and vacuoles. As shown in the figure, the fiber diameters include 9.7 µm, 11.8 µm, 10.6 µm, and 8.1 µm or between 8 and 12 µm. The vacuoles range in diameter between 15.7 µm, 68 µm, and 73.5 µm based upon the indicated measurement points. As discussed above, the diameters of the vacuoles are multiples of the fiber diameters.

Figure 10:
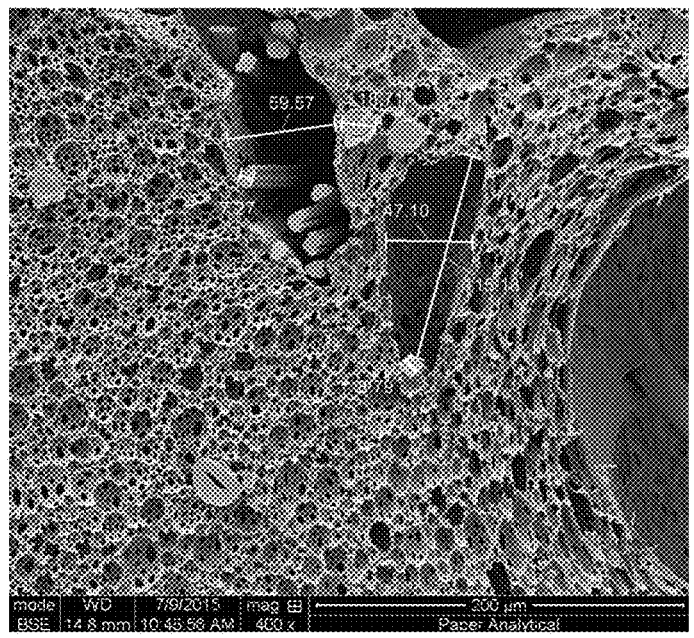
FIG. 10 is the SEM of FIG. 6 including measurements.

FIG. 10 shows the SEM of FIG. 6 with measurements on both fibers and vacuoles. As shown in the figure, the fiber diameters include 7.3 µm, 8.8 µm, and 18.7 µm, or between 7 and 20 µm. As shown in the figure, measurements have been taken within the vacuoles. In one of the vacuoles, measurements have been taken along the length and width of the cross section. In the other, vacuole, a measurement was taken along the width. Based upon the calculations, it is evident that the cross surface area of each of the vacuoles is a multiple of the fiber diameters.

Dependent upon the desired foam density, polymer composition, specific surface area, or pore-size (also referred to as cell size), the open-celled foam may be made with different chemical composition, physical properties, or both. For instance, dependent upon the chemical composition, an open-celled foam may have a density of 0.0010 g/cc to about 0.25 g/cc, or from 0.002 g/cc to about 0.2 g/cc, or from about 0.005 g/cc to about 0.15 g/cc, or from about 0.01 g/cc to about 0.1 g/cc, or from about 0.02 g/cc to about 0.08 g/cc, or about 0.04 g/cc.

Open-cell foam pore-sizes may range in average diameter of from 1 to 800 µm, such as, for example, between 50 and 700 µm, between 100 and 600 µm, between 200 and 500 µm, between 300 and 400 µm.

The foam pieces may have a relatively uniform cell size. For example, the average cell size on one major surface may be about the same or vary by no greater than 10% as compared to the opposing major surface. The average cell size of one major surface of the foam may differ from the opposing surface. For example, in the foaming of a thermosetting material it is not uncommon for a portion of the cells at the bottom of the cell structure to collapse resulting in a lower average cell size on one surface. The cell size may be determined based upon the method found below.

The foams produced from the present invention are relatively open-celled. This refers to the individual cells or pores of the foam being in substantially unobstructed communication with adjoining cells. The cells in such substantially open-celled foam structures have intercellular openings or windows that are large enough to permit ready fluid transfer from one cell to another within the foam structure. For purpose of the present invention, a foam is considered "open-celled" if at least about 80% of the cells in the foam that are at least 1 µm in average diameter size are in fluid communication with at least one adjoining cell.

In addition to being open-celled, the foams may be sufficiently hydrophilic to permit the foam to absorb aqueous fluids, for example the internal surfaces of a foam may be rendered hydrophilic by residual hydrophilizing surfactants or salts left in the foam following polymerization, by selected post-polymerization foam treatment procedures (as described hereafter), or combinations of both.

For example when used in certain absorbent articles, an open-cell foam may be flexible and exhibit an appropriate glass transition temperature (Tg). The Tg represents the midpoint of the transition between the glassy and rubbery states of the polymer.

The Tg of a region may be less than about 200° C. for foams used at about ambient temperature conditions, or less than about 90° C. The Tg may be less than 50° C.

The open-cell foam pieces may be distributed in any suitable manner throughout the heterogeneous mass. The open-cell foam pieces may be profiled along the vertical axis such that smaller pieces are located above larger pieces. Alternatively, the pieces may be profiled such that smaller pieces are below larger pieces. The open-cell pieces may be profiled along a vertical axis such that they alternate in size along the axis.

The open-cell foam pieces may be profiled along the longitudinal axis such that smaller pieces are located in front of larger pieces. Alternatively, the pieces may be profiled such that smaller pieces are behind larger pieces. The open-cell pieces may be profiled along a longitudinal axis such that they alternate in size along the axis.

The open-cell foam pieces may be profiled along the lateral axis such the size of the pieces goes from small to large or from large to small along the lateral axis. Alternatively, the open-cell pieces may be profiled along a lateral axis such that they alternate in size along the axis.

The open-cell foam pieces may be profiled along any one of the longitudinal, lateral, or vertical axis based on one or more characteristics of the open-cell foam pieces. Characteristics by which the open-cell foam pieces may be profiled within the heterogeneous mass may include, for example, absorbency, density, cell size, and combinations thereof.

The open-cell foam pieces may be profiled along any one of the longitudinal, lateral, or vertical axis based on the composition of the open-cell foam. The open-cell foam pieces may have one composition exhibiting desirable characteristics in the front of the heterogeneous mass and a different composition in the back of the heterogeneous mass designed to exhibit different characteristics. The profiling of the open-cell foam pieces may be either symmetric or asymmetric about any of the prior mentioned axes or orientations.

The open-cell foam pieces may be distributed along the longitudinal and lateral axis of the heterogeneous mass in any suitable form. The open-cell foam pieces may be distributed in a manner that forms a design or shape when viewed from a top planar view. The open-cell foam pieces may be distributed in a manner that forms stripes, ellipticals, squares, or any other known shape or pattern.

The distribution may be optimized dependent on the intended use of the heterogeneous mass. For example, a different distribution may be chosen for the absorption of aqueous fluids such as urine when used in a diaper or water when used in a paper towel versus for the absorption of a proteinaceous fluid such as menses. Further, the distribution may be optimized for uses such as dosing an active or to use the foam as a reinforcing element.

Different types of foams may be used in one heterogeneous mass. For example, some of the foam pieces may be polymerized HIPE while other pieces may be made from polyurethane. The pieces may be located at specific locations within the mass based on their properties to optimize the performance of the heterogeneous mass.

The foam pieces may be similar in composition yet exhibit different properties. For example, using HIPE foam, some foam pieces may be thin until wet while others may have been expanded within the heterogeneous mass.

The foam pieces and enrobeable elements may be selected to complement each other. For example, a foam that exhibits high permeability with low capillarity may enrobe an element that exhibits high capillarity to wick the fluid through the heterogeneous mass. It is understood that other combinations may be possible wherein the foam pieces complement each other or wherein the foam pieces and enrobeable elements both exhibit similar properties.

Profiling may occur using more than one heterogeneous mass with each heterogeneous mass having one or more types of foam pieces. The plurality of heterogeneous masses may be layered so that the foam is profiled along any one of the longitudinal, lateral, or vertical axis based on one or more characteristics of the open-cell foam pieces for an overall product that contains the plurality of heterogeneous masses. Further, each heterogeneous mass may have a different enrobeable element to which the foam is attached. For example, a first heterogeneous mass may have foam particles enrobing a nonwoven while a second heterogeneous mass adjacent the first heterogeneous mass may have foam particles enrobing a film or one surface of a film.

The open-celled foam may be a thermoset polymeric foam made from the polymerization of a High Internal Phase Emulsion (HIPE), also referred to as a polyHIPE. To form a HIPE, an aqueous phase and an oil phase are combined in a ratio between about 8:1 and 140:1. The aqueous phase to oil phase ratio may be between about 10:1 and about 75:1, and the aqueous phase to oil phase ratio may be between about 13:1 and about 65:1. This is termed the "water-to-oil" or W:O ratio and may be used to determine the density of the resulting polyHIPE foam. As discussed, the oil phase may contain one or more of monomers, comonomers, photoinitiators, crosslinkers, and emulsifiers, as well as optional components. The water phase may contain water and one or more components such as electrolyte, initiator, or optional components.

The open-cell foam may be formed from the combined aqueous and oil phases by subjecting these combined phases to shear agitation in a mixing chamber or mixing zone. The combined aqueous and oil phases are subjected to shear agitation to produce a stable HIPE having aqueous droplets of the desired size. An initiator may be present in the aqueous phase, or an initiator may be introduced during the foam making process, or after the HIPE has been formed. The emulsion making process produces a HIPE where the aqueous phase droplets are dispersed to such an extent that the resulting HIPE foam will have the desired structural characteristics. Emulsification of the aqueous and oil phase combination in the mixing zone may involve the use of a mixing or agitation device such as an impeller, by passing the combined aqueous and oil phases through a series of static mixers at a rate necessary to impart the requisite shear, or combinations of both. Once formed, the HIPE may then be withdrawn or pumped from the mixing zone. One method for forming HIPEs using a continuous process is described in U.S. Pat. No. 5,149,720 (DesMarais et al) issued Sep. 22, 1992; U.S. Pat. No. 5,827,909 (DesMarais) issued Oct. 27, 1998; and U.S. Pat. No. 6,369,121 (Catalfamo et al.) issued Apr. 9, 2002.

The emulsion may be withdrawn or pumped from the mixing zone and impregnated into or onto a mass prior to being fully polymerized. Once fully polymerized, the foam pieces and the elements are intertwined such that discrete foam pieces are bisected by the elements comprising the mass and such that parts of discrete foam pieces enrobe portions of one or more of the elements comprising the heterogeneous mass.

Following polymerization, the resulting foam pieces are saturated with aqueous phase that needs to be removed to obtain substantially dry foam pieces. Foam pieces may be squeezed free of most of the aqueous phase by using compression, for example by running the heterogeneous mass comprising the foam pieces through one or more pairs of nip rollers. The nip rollers may be positioned such that they squeeze the aqueous phase out of the foam pieces. The nip rollers may be porous and have a vacuum applied from the inside such that they assist in drawing aqueous phase out of the foam pieces. Nip rollers may be positioned in pairs, such that a first nip roller is located above a liquid permeable belt, such as a belt having pores or composed of a mesh-like material and a second opposing nip roller facing the first nip roller and located below the liquid permeable belt. One of the pair, for example the first nip roller may be pressurized while the other, for example the second nip roller, may be evacuated, so as to both blow and draw the aqueous phase out the of the foam. The nip rollers may also be heated to assist in removing the aqueous phase. Nip rollers may be applied to non-rigid foams, that is, foams whose walls would not be destroyed by compressing the foam pieces.

In place of or in combination with nip rollers, the aqueous phase may be removed by sending the foam pieces through a drying zone where it is heated, exposed to a vacuum, or a combination of heat and vacuum exposure. Heat may be applied, for example, by running the foam though a forced air oven, IR oven, microwave oven or radiowave oven. The extent to which a foam is dried depends on the application. Greater than 50% of the aqueous phase may be removed. Greater than 90%, and in still other embodiments greater than 95% of the aqueous phase may be removed during the drying process.

Open-cell foam may be produced from the polymerization of the monomers having a continuous oil phase of a High Internal Phase Emulsion (HIPE). The HIPE may have two phases. One phase is a continuous oil phase having monomers that are polymerized to form a HIPE foam and an emulsifier to help stabilize the HIPE. The oil phase may also include one or more photoinitiators. The monomer component may be present in an amount of from about 80% to about 99%, and in certain embodiments from about 85% to about 95% by weight of the oil phase. The emulsifier component, which is soluble in the oil phase and suitable for forming a stable water-in-oil emulsion may be present in the oil phase in an amount of from about 1% to about 20% by weight of the oil phase. The emulsion may be formed at an emulsification temperature of from about 10° C. to about 130° C. and in certain embodiments from about 50° C. to about 100° C.

In general, the monomers will include from about 20% to about 97% by weight of the oil phase at least one substantially water-insoluble monofunctional alkyl acrylate or alkyl methacrylate. For example, monomers of this type may include $C_4$-$C_{18}$ alkyl acrylates and $C_2$-$C_{18}$ methacrylates, such as ethylhexyl acrylate, butyl acrylate, hexyl acrylate, octyl acrylate, nonyl acrylate, decyl acrylate, isodecyl acrylate, tetradecyl acrylate, benzyl acrylate, nonyl phenyl acrylate, hexyl methacrylate, 2-ethylhexyl methacrylate, octyl methacrylate, nonyl methacrylate, decyl methacrylate, isodecyl methacrylate, dodecyl methacrylate, tetradecyl methacrylate, and octadecyl methacrylate.

The oil phase may also have from about 2% to about 40%, and in certain embodiments from about 10% to about 30%, by weight of the oil phase, a substantially water-insoluble, polyfunctional crosslinking alkyl acrylate or methacrylate. This crosslinking comonomer, or crosslinker, is added to confer strength and resilience to the resulting HIPE foam. Examples of crosslinking monomers of this type may have monomers containing two or more activated acrylate, methacrylate groups, or combinations thereof. Nonlimiting examples of this group include 1,6-hexanedioldiacrylate, 1,4-butanedioldimethacrylate, trimethylolpropane triacrylate, trimethylolpropane trimethacrylate, 1,12-dodecyldimethacrylate, 1,14-tetradecanedioldimethacrylate, ethylene glycol dimethacrylate, neopentyl glycol diacrylate (2,2-dimethylpropanediol diacrylate), hexanediol acrylate methacrylate, glucose pentaacrylate, sorbitan pentaacrylate, and the like. Other examples of crosslinkers contain a mixture of acrylate and methacrylate moieties, such as ethylene glycol acrylate-methacrylate and neopentyl glycol acrylate-methacrylate. The ratio of methacrylate:acrylate group in the mixed crosslinker may be varied from 50:50 to any other ratio as needed.

Any third substantially water-insoluble comonomer may be added to the oil phase in weight percentages of from about 0% to about 15% by weight of the oil phase, in certain embodiments from about 2% to about 8%, to modify properties of the HIPE foams. "Toughening" monomers may be desired which impart toughness to the resulting HIPE foam. These include monomers such as styrene, vinyl chloride, vinylidene chloride, isoprene, and chloroprene. Without being bound by theory, it is believed that such monomers aid in stabilizing the HIPE during polymerization (also known as "curing") to provide a more homogeneous and better formed HIPE foam which results in better toughness, tensile strength, abrasion resistance, and the like. Monomers may also be added to confer flame retardancy as disclosed in U.S. Pat. No. 6,160,028 (Dyer) issued Dec. 12, 2000. Monomers may be added to confer color, for example vinyl ferrocene, fluorescent properties, radiation resistance, opacity to radiation, for example lead tetraacrylate, to disperse charge, to reflect incident infrared light, to absorb radio waves, to form a wettable surface on the HIPE foam struts, or for any other desired property in a HIPE foam. In some cases, these additional monomers may slow the overall process of conversion of HIPE to HIPE foam, the tradeoff being necessary if the desired property is to be conferred. Thus, such monomers may be used to slow down the polymerization rate of a HIPE. Examples of monomers of this type may have styrene and vinyl chloride.

The oil phase may further contain an emulsifier used for stabilizing the HIPE. Emulsifiers used in a HIPE may include: (a) sorbitan monoesters of branched $C_{16}$-$C_{24}$ fatty acids; linear unsaturated $C_{16}$-$C_{22}$ fatty acids; and linear saturated $C_{12}$-$C_{14}$ fatty acids, such as sorbitan monooleate, sorbitan monomyristate, and sorbitan monoesters, sorbitan monolaurate diglycerol monooleate (DGMO), polyglycerol monoisostearate (PGMIS), and polyglycerol monomyristate (PGMM); (b) polyglycerol monoesters of -branched $C_{16}$-$C_{24}$ fatty acids, linear unsaturated $C_{16}$-$C_{22}$ fatty acids, or linear saturated $C_{12}$-$C_{14}$ fatty acids, such as diglycerol monooleate (for example diglycerol monoesters of C18:1 fatty acids), diglycerol monomyristate, diglycerol monoisostearate, and diglycerol monoesters; (c) diglycerol monoaliphatic ethers of -branched $C_{16}$-$C_{24}$ alcohols, linear unsaturated $C_{16}$-$C_{22}$ alcohols, and linear saturated $C_{12}$-$C_{14}$ alcohols, and mixtures of these emulsifiers. See U.S. Pat. No. 5,287,207 (Dyer et al.), issued Feb. 7, 1995 and U.S. Pat. No. 5,500,451 (Goldman et al.) issued Mar. 19, 1996. Another emulsifier that may be used is polyglycerol succinate (PGS), which is formed from an alkyl succinate, glycerol, and triglycerol.

Such emulsifiers, and combinations thereof, may be added to the oil phase so that they may have between about 1% and about 20%, in certain embodiments from about 2% to about 15%, and in certain other embodiments from about 3% to about 12% by weight of the oil phase. Coemulsifiers may also be used to provide additional control of cell size, cell size distribution, and emulsion stability, particularly at higher temperatures, for example greater than about 65° C. Examples of coemulsifiers include phosphatidyl cholines and phosphatidyl choline-containing compositions, aliphatic betaines, long chain $C_{12}$-$C_{22}$ dialiphatic quaternary ammonium salts, short chain $C_1$-$C_4$ dialiphatic quaternary ammonium salts, long chain $C_{12}$-$C_{22}$ dialkoyl(alkenoyl)-2-hydroxyethyl, short chain $C_1$-$C_4$ dialiphatic quaternary ammonium salts, long chain $C_{12}$-$C_{22}$ dialiphatic imidazolinium quaternary ammonium salts, short chain $C_1$-$C_4$ dialiphatic imidazolinium quaternary ammonium salts, long chain $C_{12}$-$C_{22}$ monoaliphatic benzyl quaternary ammonium salts, long chain $C_{12}$-$C_{22}$ dialkoyl(alkenoyl)-2-aminoethyl, short chain $C_1$-$C_4$ monoaliphatic benzyl quaternary ammonium salts, short chain $C_1$-$C_4$ monohydroxyaliphatic quaternary ammonium salts. Ditallow dimethyl ammonium methyl sulfate (DTDMAMS) may be used as a coemulsifier.

The oil phase may comprise a photoinitiator at between about 0.05% and about 10%, and in certain embodiments between about 0.2% and about 10% by weight of the oil phase. Lower amounts of photoinitiator allow light to better penetrate the HIPE foam, which may provide for polymerization deeper into the HIPE foam. However, if polymerization is done in an oxygen-containing environment, there should be enough photoinitiator to initiate the polymerization and overcome oxygen inhibition. Photoinitiators may respond rapidly and efficiently to a light source with the production of radicals, cations, and other species that are capable of initiating a polymerization reaction. The photoinitiators used in the present invention may absorb UV light at wavelengths of about 200 nanometers (nm) to about 800 nm, in certain embodiments about 200 nm to about 350 nm. If the photoinitiator is in the oil phase, suitable types of oil-soluble photoinitiators include benzyl ketals, α-hydroxyalkyl phenones, α-amino alkyl phenones, and acylphospine oxides. Examples of photoinitiators include 2,4,6-[trimethylbenzoyldiphosphine] oxide in combination with 2-hydroxy-2-methyl-1-phenylpropan-1-one (50:50 blend of the two is sold by Ciba Speciality Chemicals, Ludwigshafen, Germany as DAROCUR® 4265); benzyl dimethyl ketal (sold by Ciba Geigy as IRGACURE 651); α-,α-dimethoxy-α-hydroxy acetophenone (sold by Ciba Speciality Chemicals as DAROCUR® 1173); 2-methyl-1-[4-(methyl thio) phenyl]-2-morpholino-propan-1-one (sold by Ciba Speciality Chemicals as IRGACURE® 907); 1-hydroxycyclohexyl-phenyl ketone (sold by Ciba Speciality Chemicals as IRGACURE® 184); bis(2,4,6-trimethylbenzoyl)-phenylphosphineoxide (sold by Ciba Speciality Chemicals as IRGACURE 819); diethoxyacetophenone, and 4-(2-hydroxyethoxy)phenyl-(2-hydroxy-2-methylpropyl) ketone (sold by Ciba Speciality Chemicals as IRGACURE® 2959); and Oligo [2-hydroxy-2-methyl-1-[4-(1-methylvinyl) phenyl]propanone] (sold by Lamberti spa, Gallarate, Italy as ESACURE® KIP EM.

The dispersed aqueous phase of a HIPE may have water, and may also have one or more components, such as initiator, photoinitiator, or electrolyte, wherein in certain embodiments, the one or more components are at least partially water soluble.

One component of the aqueous phase may be a water-soluble electrolyte. The water phase may contain from about 0.2% to about 40%, in certain embodiments from about 2% to about 20%, by weight of the aqueous phase of a water-soluble electrolyte. The electrolyte minimizes the tendency of monomers, comonomers, and crosslinkers that are primarily oil soluble to also dissolve in the aqueous phase. Examples of electrolytes include chlorides or sulfates of alkaline earth metals such as calcium or magnesium and chlorides or sulfates of alkali earth metals such as sodium. Such electrolyte may include a buffering agent for the control of pH during the polymerization, including such inorganic counterions as phosphate, borate, and carbonate, and mixtures thereof. Water soluble monomers may also be used in the aqueous phase, examples being acrylic acid and vinyl acetate.

Another component that may be present in the aqueous phase is a water-soluble free-radical initiator. The initiator may be present at up to about 20 mole percent based on the total moles of polymerizable monomers present in the oil phase. The initiator may be present in an amount of from about 0.001 to about 10 mole percent based on the total moles of polymerizable monomers in the oil phase. Suitable initiators include ammonium persulfate, sodium persulfate, potassium persulfate, 2,2'-azobis(N,N'-dimethyleneisobutyramidine)dihydrochloride, and other suitable azo initiators. To reduce the potential for premature polymerization which may clog the emulsification system, addition of the initiator to the monomer phase may be just after or near the end of emulsification.

Photoinitiators present in the aqueous phase may be at least partially water soluble and may have between about 0.05% and about 10%, and in certain embodiments between about 0.2% and about 10% by weight of the aqueous phase. Lower amounts of photoinitiator allow light to better penetrate the HIPE foam, which may provide for polymerization deeper into the HIPE foam. However, if polymerization is done in an oxygen-containing environment, there should be enough photoinitiator to initiate the polymerization and overcome oxygen inhibition. Photoinitiators may respond rapidly and efficiently to a light source with the production of radicals, cations, and other species that are capable of initiating a polymerization reaction. The photoinitiators used in the present invention may absorb UV light at wavelengths of from about 200 nanometers (nm) to about 800 nm, in certain embodiments from about 200 nm to about 350 nm, and in certain embodiments from about 350 nm to about 450 nm. If the photoinitiator is in the aqueous phase, suitable types of water-soluble photoinitiators include benzophenones, benzils, and thioxanthones. Examples of photoinitiators include 2,2'-Azobis[2-(2-imidazolin-2-yl)propane]dihydrochloride; 2,2'-Azobis[2-(2-imidazolin-2-yl)propane] disulfate dehydrate; 2,2'-Azobis(1-imino-1-pyrrolidino-2-ethylpropane)dihydrochloride; 2,2'-Azobis[2-methyl-N-(2-hydroxyethyl)propionamide]; 2,2'-Azobis(2-methylpropionamidine)dihydrochloride; 2,2'-dicarboxymethoxydibenzalacetone, 4,4'-dicarboxymethoxydibenzalacetone, 4,4'-dicarboxymethoxydibenzalcyclohexanone, 4-dimethylamino-4'-carboxymethoxydibenzalacetone; and 4,4'-disulphoxymethoxydibenzalacetone. Other suitable photoinitiators that may be used in the present invention are listed in U.S. Pat. No. 4,824,765 (Sperry et al.) issued Apr. 25, 1989.

In addition to the previously described components other components may be included in either the aqueous or oil phase of a HIPE. Examples include antioxidants, for example hindered phenolics, hindered amine light stabilizers; plasticizers, for example dioctyl phthalate, dinonyl sebacate; flame retardants, for example halogenated hydrocarbons, phosphates, borates, inorganic salts such as antimony trioxide or ammonium phosphate or magnesium hydroxide; dyes and pigments; fluorescers; filler pieces, for example starch, titanium dioxide, carbon black, or calcium carbonate; fibers; chain transfer agents; odor absorbers, for example activated carbon particulates; dissolved polymers; dissolved oligomers; and the like.

The heterogeneous mass comprises enrobeable elements and discrete pieces of foam. The enrobeable elements may be a web such as, for example, nonwoven, a fibrous structure, an airlaid web, a wet laid web, a high loft nonwoven, a needlepunched web, a hydroentangled web, a fiber tow, a woven web, a knitted web, a flocked web, a spunbond web, a layered spunbond/melt blown web, a carded fiber web, a coform web of cellulose fiber and melt blown fibers, a coform web of staple fibers and melt blown fibers, and layered webs that are layered combinations thereof.

The enrobeable elements may be, for example, conventional absorbent materials such as creped cellulose wadding, fluffed cellulose fibers, wood pulp fibers also known as airfelt, and textile fibers. The enrobeable elements may also be fibers such as, for example, synthetic fibers, thermoplastic particulates or fibers, tricomponent fibers, and bicomponent fibers such as, for example, sheath/core fibers having the following polymer combinations: polyethylene/polypropylene, polyethylvinyl acetate/polypropylene, polyethylene/polyester, polypropylene/polyester, copolyester/polyester, and the like. The enrobeable elements may be any combination of the materials listed above and/or a plurality of the materials listed above, alone or in combination.

The enrobeable elements may be hydrophobic or hydrophilic. The enrobeable elements may be treated to be made hydrophobic. The enrobeable elements may be treated to become hydrophilic.

The constituent fibers of the heterogeneous mass may be comprised of polymers such as polyethylene, polypropylene, polyester, and blends thereof. The fibers may be spunbound fibers. The fibers may be meltblown fibers. The fibers may comprise cellulose, rayon, cotton, or other natural materials or blends of polymer and natural materials. The fibers may also comprise a super absorbent material such as polyacrylate or any combination of suitable materials. The fibers may be monocomponent, bicomponent, and/or biconstituent, non-round (e.g., capillary channel fibers), and may have major cross-sectional dimensions (e.g., diameter for round fibers) ranging from 0.1-500 microns. The constituent fibers of the nonwoven precursor web may also be a mixture of different fiber types, differing in such features as chemistry (e.g. polyethylene and polypropylene), components (mono- and bi-), denier (micro denier and >20 denier), shape (i.e. capillary and round) and the like. The constituent fibers may range from about 0.1 denier to about 100 denier.

In one aspect, known absorbent web materials in an as-made may be considered as being homogeneous throughout. Being homogeneous, the fluid handling properties of the absorbent web material are not location dependent, but are substantially uniform at any area of the web. Homogeneity may be characterized by density, basis weight, for example, such that the density or basis weight of any particular part of the web is substantially the same as an average density or basis weight for the web. By the apparatus and method of the present invention, homogeneous fibrous absorbent web materials are modified such that they are no longer homogeneous, but are heterogeneous, such that the fluid handling properties of the web material are location dependent. Therefore, for the heterogeneous absorbent materials of the present invention, at discrete locations the density or basis weight of the web may be substantially different than the average density or basis weight for the web. The heterogeneous nature of the absorbent web of the present invention permits the negative aspects of either of permeability or capillarity to be minimized by rendering discrete portions highly permeable and other discrete portions to have high capillarity. Likewise, the tradeoff between permeability and capillarity is managed such that delivering relatively higher permeability may be accomplished without a decrease in capillarity.

The heterogeneous mass may also include superabsorbent material that imbibe fluids and form hydrogels. These materials are typically capable of absorbing large quantities of body fluids and retaining them under moderate pressures. The heterogeneous mass may include such materials dispersed in a suitable carrier such as cellulose fibers in the form of fluff or stiffened fibers.

The heterogeneous mass may include thermoplastic particulates or fibers. The materials, and in particular thermoplastic fibers, may be made from a variety of thermoplastic polymers including polyolefins such as polyethylene (e.g., PULPEX®) and polypropylene, polyesters, copolyesters, and copolymers of any of the foregoing.

Depending upon the desired characteristics, suitable thermoplastic materials include hydrophobic fibers that have been made hydrophilic, such as surfactant-treated or silica-treated thermoplastic fibers derived from, for example, polyolefins such as polyethylene or polypropylene, polyacrylics, polyamides, polystyrenes, and the like. The surface of the hydrophobic thermoplastic fiber may be rendered hydrophilic by treatment with a surfactant, such as a nonionic or anionic surfactant, e.g., by spraying the fiber with a surfactant, by dipping the fiber into a surfactant or by including the surfactant as part of the polymer melt in producing the thermoplastic fiber. Upon melting and resolidification, the surfactant will tend to remain at the surfaces of the thermoplastic fiber. Suitable surfactants include nonionic surfactants such as Brij 76 manufactured by ICI Americas, Inc. of Wilmington, Del., and various surfactants sold under the Pegosperse® trademark by Glyco Chemical, Inc. of Greenwich, Conn. Besides nonionic surfactants, anionic surfactants may also be used. These surfactants may be applied to the thermoplastic fibers at levels of, for example, from about 0.2 to about 1 g. per sq. of centimeter of thermoplastic fiber.

Suitable thermoplastic fibers may be made from a single polymer (monocomponent fibers), or may be made from more than one polymer (e.g., bicomponent fibers). The polymer comprising the sheath often melts at a different, typically lower, temperature than the polymer comprising the core. As a result, these bicomponent fibers provide thermal bonding due to melting of the sheath polymer, while retaining the desirable strength characteristics of the core polymer.

Suitable bicomponent fibers for use in the present invention may include sheath/core fibers having the following polymer combinations: polyethylene/polypropylene, polyethylvinyl acetate/polypropylene, polyethylene/polyester, polypropylene/polyester, copolyester/polyester, and the like. Particularly suitable bicomponent thermoplastic fibers for use herein are those having a polypropylene or polyester core, and a lower melting copolyester, polyethylvinyl acetate or polyethylene sheath (e.g., DANAKLON®, CELBOND® or CHISSO® bicomponent fibers). These bicomponent fibers may be concentric or eccentric. As used herein, the terms "concentric" and "eccentric" refer to whether the sheath has a thickness that is even, or uneven, through the cross-sectional area of the bicomponent fiber. Eccentric bicomponent fibers may be desirable in providing more compressive strength at lower fiber thicknesses. Suitable bicomponent fibers for use herein may be either uncrimped (i.e. unbent) or crimped (i.e. bent). Bicomponent fibers may be crimped by typical textile means such as, for example, a stuffer box method or the gear crimp method to achieve a predominantly two-dimensional or "flat" crimp.

The length of bicomponent fibers may vary depending upon the particular properties desired for the fibers and the web formation process. Typically, in an airlaid web, these thermoplastic fibers have a length from about 2 mm to about 12 mm long such as, for example, from about 2.5 mm to about 7.5 mm long, and from about 3.0 mm to about 6.0 mm long. Nonwoven fibers may be between 5 mm long and 75 mm long, such as, for example, 10 mm long, 15 mm long, 20 mm long, 25 mm long, 30 mm long, 35 mm long, 40 mm long, 45 mm long, 50 mm long, 55 mm long, 60 mm long, 65 mm long, or 70 mm long. The properties-of these thermoplastic fibers may also be adjusted by varying the diameter (caliper) of the fibers. The diameter of these thermoplastic fibers is typically defined in terms of either denier (grams per 9000 meters) or decitex (grams per 10,000 meters). Suitable bicomponent thermoplastic fibers as used in an airlaid making machine may have a decitex in the range from about 1.0 to about 20 such as, for example, from about 1.4 to about 10, and from about 1.7 to about 7 decitex.

The compressive modulus of these thermoplastic materials, and especially that of the thermoplastic fibers, may also be important. The compressive modulus of thermoplastic fibers is affected not only by their length and diameter, but also by the composition and properties of the polymer or polymers from which they are made, the shape and configuration of the fibers (e.g., concentric or eccentric, crimped or uncrimped), and like factors. Differences in the compressive modulus of these thermoplastic fibers may be used to alter the properties, and especially the density characteristics, of the respective thermally bonded fibrous matrix.

The heterogeneous mass may also include synthetic fibers that typically do not function as binder fibers but alter the mechanical properties of the fibrous webs. Synthetic fibers include cellulose acetate, polyvinyl fluoride, polyvinylidene chloride, acrylics (such as Orlon), polyvinyl acetate, non-soluble polyvinyl alcohol, polyethylene, polypropylene, polyamides (such as nylon), polyesters, bicomponent fibers, tricomponent fibers, mixtures thereof and the like. These might include, for example, polyester fibers such as polyethylene terephthalate (e.g., DACRON® and KODEL®), high melting crimped polyester fibers (e.g., KODEL® 431 made by Eastman Chemical Co.) hydrophilic nylon (HYDROFIL®), and the like. Suitable fibers may also hydrophilized hydrophobic fibers, such as surfactant-treated or silica-treated thermoplastic fibers derived from, for example, polyolefins such as polyethylene or polypropylene, polyacrylics, polyamides, polystyrenes, polyurethanes and the like. In the case of nonbonding thermoplastic fibers, their length may vary depending upon the particular properties desired for these fibers. Typically they have a length from about 0.3 to 7.5 cm, such as, for example from about 0.9 to about 1.5 cm. Suitable nonbonding thermoplastic fibers may have a decitex in the range of about 1.5 to about 35 decitex, such as, for example, from about 14 to about 20 decitex.

However structured, the total absorbent capacity of the heterogeneous mass containing foam pieces should be compatible with the design loading and the intended use of the mass. For example, when used in an absorbent article, the size and absorbent capacity of the heterogeneous mass may be varied to accommodate different uses such as incontinence pads, pantiliners, regular sanitary napkins, or overnight sanitary napkins. The heterogeneous mass may also include other optional components sometimes used in absorbent webs. For example, a reinforcing scrim may be positioned within the respective layers, or between the respective layers, of the heterogeneous mass.

The heterogeneous mass comprising open-cell foam pieces produced from the present invention may be used as an absorbent core or a portion of an absorbent core in absorbent articles, such as feminine hygiene articles, for example pads, pantiliners, and tampons; disposable diapers; incontinence articles, for example pads, adult diapers; homecare articles, for example wipes, pads, towels; and beauty care articles, for example pads, wipes, and skin care articles, such as used for pore cleaning.

The heterogeneous mass may be used as an absorbent core for an absorbent article. The absorbent core may be relatively thin, less than about 5 mm in thickness, or less than about 3 mm, or less than about 1 mm in thickness. Cores having a thickness of greater than 5 mm are also contemplated herein. Thickness may be determined by measuring the thickness at the midpoint along the longitudinal centerline of the absorbent structure by any means known in the art for doing while under a uniform pressure of 0.25 psi. The absorbent core may comprise absorbent gelling materials (AGM), including AGM fibers, as is known in the art.

The heterogeneous mass may be formed or cut to a shape, the outer edges of which define a periphery. Additionally, the heterogeneous mass may be continuous such that it may be rolled or wound upon itself, with or without the inclusion of preformed cut lines demarcating the heterogeneous mass into preformed sections.

When used as an absorbent core, the shape of the heterogeneous mass may be generally rectangular, circular, oval, elliptical, or the like. Absorbent core may be generally centered with respect to the longitudinal centerline and transverse centerline of an absorbent article. The profile of absorbent core may be such that more absorbent is disposed near the center of the absorbent article. For example, the absorbent core may be thicker in the middle, and tapered at the edges in a variety of ways known in the art.

The absorbent structure single stratum may serve as any portion of an absorbent article. The absorbent structure single stratum may serve as the absorbent core of an absorbent article. The absorbent structure single stratum may serve as a portion of the absorbent core of an absorbent article. More than one absorbent structure single stratum may be combined wherein each absorbent structure single stratum differs from at least one other absorbent structure single stratum in either the choice of enrobeable elements or by a characteristic of its open-cell foam pieces. The different two or more absorbent structures single stratums may be combined to form an absorbent core. The absorbent article may further comprise a topsheet and a backsheet.

The absorbent structure single stratum may be used as a topsheet for an absorbent article. The absorbent structure single stratum may be combined with an absorbent core or may only be combined with a backsheet.

The absorbent structure single stratum may be combined with any other type of absorbent layer such as, for example, a storage or acquisition layer comprising a layer of cellulose, a layer comprising superabsorbent gelling materials, a layer of absorbent airlaid fibers, or a layer of absorbent foam. Other absorbent layers not listed are contemplated herein.

The absorbent structure single stratum may be utilized by itself for the absorption of fluids without placing it into an absorbent article.

An absorbent article may comprise a liquid pervious topsheet. The topsheet suitable for use herein may comprise wovens, non-wovens, and/or three-dimensional webs of a liquid impermeable polymeric film comprising liquid permeable apertures. The topsheet for use herein may be a single layer or may have a multiplicity of layers. For example, the wearer-facing and contacting surface may be provided by a film material having apertures which are provided to facilitate liquid transport from the wearer facing surface towards the absorbent structure. Such liquid permeable, apertured films are well known in the art. They provide a resilient three-dimensional fibre-like structure. Such films have been disclosed in detail for example in U.S. Pat. Nos. 3,929,135, 4,151,240, 4,319,868, 4,324,426, 4,343,314, 4,591,523, 4,609,518, 4,629,643, 4,695,422 or WO 96/00548.

The absorbent articles of FIGS. 1 to 11 comprising embodiments of the absorbent structure may also comprise a backsheet and a topsheet. The backsheet may be used to prevent the fluids absorbed and contained in the absorbent structure from wetting materials that contact the absorbent article such as underpants, pants, pyjamas, undergarments, and shirts or jackets, thereby acting as a barrier to fluid transport. The backsheet may also allow the transfer of at least water vapour, or both water vapour and air through it.

Especially when the absorbent article finds utility as a sanitary napkin or panty liner, the absorbent article may be also provided with a panty fastening means, which provides means to attach the article to an undergarment, for example a panty fastening adhesive on the garment facing surface of the backsheet. Wings or side flaps meant to fold around the crotch edge of an undergarment may be also provided on the side edges of the napkin.

EXAMPLES

A. A heterogeneous mass comprising a longitudinal axis, a lateral axis, a vertical axis, two or more enrobeable elements and one or more discrete open cell foam pieces wherein at least one of the discrete open cell foam pieces comprises a first vacuole, wherein the first vacuole has a first cross sectional area, wherein the first vacuole enrobes a first enrobeable element, wherein the first enrobeable element and the second enrobeable element exhibit different surface properties or physical geometries.

B. The heterogeneous mass according to paragraph A, wherein one of the first enrobeable element or second enrobeable element comprises a surfactant coating.

C. The heterogeneous mass according to paragraph B, wherein the surfactant coating is selected from the group consisting of an anionic surfactant, a cationic surfactant, a zwitterionic surfactant, a nonionic surfactant, or combinations thereof.

D. The heterogeneous mass according to any of paragraphs A-C, wherein two or more fibers are bundled and wherein a vacuole enrobes the two or more bundled fibers.

E. The heterogeneous mass according to any of paragraphs A-D, wherein the first vacuole diameter is less than two time the diameter of the first enrobeable element and wherein the first enrobeable element is coated with a nonionic surfactant.

F. The heterogeneous mass according to any of paragraphs A-E, wherein the discrete open cell foam pieces comprise HIPE foam.

G. The heterogeneous mass according to any of paragraphs A-F, wherein the at least one vacuole has an inscribed circle having a diameter that is between 1 and 10 times the diameter of the fiber.

H. The heterogeneous mass according to any of paragraphs A-G, wherein the surface properties are inherent to the enrobeable element.

I. A heterogeneous mass comprising a longitudinal axis, a lateral axis, a vertical axis, one or more enrobeable elements and one or more discrete open cell foam pieces wherein at least one of the discrete open cell foam pieces comprises a first vacuole and a second vacuole wherein the first vacuole has a first cross sectional area, wherein the second vacuole has a second cross sectional area, wherein the first vacuole enrobes a first enrobeable element, wherein the second vacuole enrobes a second enrobeable element, wherein the first enrobeable element and the second enrobeable element exhibit different surface properties or physical geometries.

J. The heterogeneous mass according to paragraph I, wherein one of the first enrobeable element or second enrobeable element comprises a surfactant coating.

K. The heterogeneous mass according to paragraph J, wherein the surfactant coating is selected from the group consisting of an anionic surfactant, a cationic surfactant, a zwitterionic surfactant, a nonionic surfactant, or combinations thereof.

L. The heterogeneous mass according to any of paragraphs I-K, wherein two or more fibers are bundled and wherein a vacuole enrobes the two or more bundled fibers.

M. The heterogeneous mass according to any of paragraphs I-L, wherein the first vacuole diameter is less than two time the diameter of the first enrobeable element and wherein the first enrobeable element is coated with a nonionic surfactant.

N. The heterogeneous mass according to any of paragraphs I-M, wherein the at least one vacuole has an inscribed circle having a diameter that is between 1 and 10 times the diameter of the fiber.

O. The heterogeneous mass according to any of paragraphs I-N, wherein the discrete open cell foam pieces comprise HIPE foam.

P. A method of creating vacuoles within a heterogeneous mass, the method comprising coating one or more enrobeable element with a surfactant to form a first coated enrobeable element, enrobing one or more enrobeable elements comprising the first coated enrobeable element with a high internal phase emulsion, polymerizing the high internal phase emulsion to form a heterogeneous mass containing a discrete open cell foam piece comprising a vacuole.

Q. The method according to paragraph P, wherein the first coated enrobeable element is coated with a surfactant selected from the group consisting of coating is selected from the group consisting of an anionic surfactant, a cationic surfactant, a zwitterionic surfactant, a nonionic surfactant, or combinations thereof.

R. The method according to paragraph P or Q, wherein the first coated enrobeable elements are selectively located in the heterogeneous mass to create a pattern.

S. The method according to paragraph R, wherein the pattern comprises stripes, a grid, a gradient pattern along a vertical axis, a gradient pattern along a lateral axis, a gradient pattern along a longitudinal axis or combinations thereof.

T. The method according to any of paragraphs P-S, wherein the one or more enrobeable elements are coated with a second surfactant to form a second coated enrobeable element having different surface properties from the first coated enrobeable element, wherein the second coated enrobeable element is coated with a surfactant selected from the group consisting of coating is selected from the group consisting of an anionic surfactant, a cationic surfactant, a zwitterionic surfactant, a nonionic surfactant, or combinations thereof.

Method for Assessing Areas for Pore Size Calculations Using SEM Imaging:

Sample Preparation

The first step is to prepare the sample to be imaged using SEM: Section of the heterogeneous mass are cut into approximately 1.5 cm×4 cm strips from the original samples. These strips are then cut the strips into sections. Each section should contain the entire composite. The strips should be cut using a razor blade, such as VWR Single Edge Industrial, 0.009" thick surgical carbon steel or equivalent, at room temperature (available from VWR Scientific, Radnor Pa., USA). Following the cutting of strips into sections, the sections are adhered to a mount using double-side Cu tape, with the-sectioned face up, and sputter Au coated.

Analysis

Secondary Electron (SE) images are obtained using an SEM, such as a FEI Quanta 450 (available from FEI Company, Hillsboro, Oreg., USA), operated in high-vacuum mode using acceleration voltages between 3 and 5 kV and a working distance of approximately 12-18 mm. This methodology assumes the analyst is skilled in SEM operation so that images with sufficient contrast are obtained.

Viewing the SEM Sample

Samples should be viewed at 25 or 50× magnification. The different pore-size ranges are distinguished by the different portions within the heterogeneous mass. Distinct portions exhibit different cell/pore sizes/open area/solid phase vs gas phase. The magnification for the portions is chosen to enable clear visualization of the portion and the ability to distinguish the solid phase from the gas phase.

Determination of portions having different pore-size ranges is done at a magnification of 25×. The heterogeneous mass SEM is divided into an upper portion and a lower portion at the point where the lowest fiber is located along the Z-direction. Each portion is then divided into three portions. This creates three portions with the first upper portion and the first lower portion sharing a boundary. The pore-size range of the upper second portion is compared to pore-size range of the lower second portion. The lower third region may be compared to the upper second region and the lower second region to determine if there is an additional pore-size range. The upper third region may be compared to the upper second region and the lower second region to determine if there is an additional pore-size range. Pore size ranges are determined on the largest ten pores in the field of view and using software that is capable of analyzing the SEM images.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Values disclosed herein as ends of ranges are not to be understood as being strictly limited to the exact numerical values recited. Instead, unless otherwise specified, each numerical range is intended to mean both the recited values and any integers within the range. For example, a range disclosed as "1 to 10" is intended to mean "1, 2, 3, 4, 5, 6, 7, 8, 9, and 10."

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A feminine hygiene article comprising an absorbent structure, the absorbent structure comprising a heterogeneous mass comprising a longitudinal axis, a lateral axis, a vertical axis, a fibrous nonwoven web comprising a plurality of enrobeable fibers and one or more discrete hydrophilic open cell HIPE foam pieces enrobing fibers of said plurality of enrobeable fibers, wherein at least one of the discrete hydrophilic open cell HIPE foam pieces comprises a first vacuole, wherein the first vacuole has a first cross sectional area, wherein the first vacuole enrobes a first enrobeable fiber, wherein the first enrobeable fiber and a second enrobeable fiber exhibit different surface properties or physical geometries, and wherein the first vacuole diameter is less than two times the diameter of the first enrobeable fiber and wherein the first enrobeable fiber is coated with a nonionic surfactant.

2. The heterogeneous mass of claim 1, wherein two or more fibers are bundled and wherein a vacuole enrobes the two or more bundled fibers.

3. The heterogeneous mass of claim 1, further comprising multiple vacuoles, wherein at least one vacuole has an inscribed circle having a diameter that is between 1 and 10 times the diameter of the fiber.

4. The heterogeneous mass of claim 1, wherein the surface properties are inherent to at least one of the first and second enrobeable fibers.

5. A feminine hygiene article comprising an absorbent structure, the absorbent structure comprising a heterogeneous mass comprising a longitudinal axis, a lateral axis, a vertical axis, a fibrous nonwoven web comprising a plurality of enrobeable fibers and one or more discrete hydrophilic open cell HIPE foam pieces enrobing fibers of said plurality of enrobeable fibers, wherein at least one of the discrete hydrophilic open cell HIPE foam pieces comprises a first vacuole and a second vacuole wherein the first vacuole has a first cross sectional area, wherein the second vacuole has a second cross sectional area, wherein the first vacuole enrobes a first enrobeable fiber, wherein the second vacuole enrobes a second enrobeable fiber, wherein the first enrobeable fiber and the second enrobeable fiber exhibit different surface properties or physical geometries, and wherein the first vacuole diameter is less than two times the diameter of the first enrobeable fiber and wherein the first enrobeable fiber is coated with a nonionic surfactant.

6. The heterogeneous mass of claim 5, wherein two or more fibers are bundled and wherein a vacuole enrobes the two or more bundled fibers.

7. The heterogeneous mass of claim 5, further comprising multiple vacuoles, wherein at least one vacuole has an inscribed circle having a diameter that is between 1 and 10 times the diameter of the fiber.

* * * * *